United States Patent [19]
Deetz et al.

[11] Patent Number: 5,853,714
[45] Date of Patent: Dec. 29, 1998

[54] METHOD FOR PURIFICATION OF IL-12

[75] Inventors: Jeffrey S. Deetz, Melrose, Mass.; Bonnie Germain, Webster, N.H.; Brian Hubbard, Newbury, Mass.; Lei Shi, Wilmington, Mass.; Thomas Spitznagel, Woburn, Mass.; Dwight Winters, Camarillo, Calif.

[73] Assignee: Genetics Institute, Inc., Cambridge, Mass.

[21] Appl. No.: 411,028

[22] Filed: Mar. 27, 1995

[51] Int. Cl.⁶ ................................................. A61K 45/05
[52] U.S. Cl. .......................... 424/85.2; 530/351; 530/414; 530/416
[58] Field of Search ............................. 530/351, 414, 530/416; 424/85.2

[56] References Cited

U.S. PATENT DOCUMENTS

| | | | |
|---|---|---|---|
| 5,338,834 | 8/1994 | Williams | 530/351 |
| 5,457,038 | 10/1995 | Trinchicin et al. | 435/69.52 |

FOREIGN PATENT DOCUMENTS

| | | |
|---|---|---|
| 433827 | 6/1991 | European Pat. Off. . |
| 9205256 | 4/1992 | WIPO . |

OTHER PUBLICATIONS

Gately et al., International Immunol. 6:157–167 (1994).
Harris et al., "Protein purification methods", IRL Press, Chapter 4, 1989.
Stein et al., PNAS, Vol. 87, pp 6806–12, 1990.
Kato, Adv. Chromatogr. pp 97–115, 1987.
Sofer et al., Biotechnique, pp.198–203, Nov/Dec. 1993.
Harris et al., "Protein Purificiation Methods" IRL Press, p 57–64, 1989.
Nahanna et al., Inf. Immun., Vol. 61(1), p 64–70, 1993.
Kobayashi et al., J. Exp. Med., Vol. 170, p 827–845, 1989.

*Primary Examiner*—Chhaya D. Sayala
*Attorney, Agent, or Firm*—Scott A. Brown; Thomas J. DesRosier

[57] ABSTRACT

Methods for the purification of interleukin-12 (IL-12) is provided.

1 Claim, 14 Drawing Sheets

METHOD FOR PURIFICATION OF IL-12

BACKGROUND OF THE INVENTION

Interleukin-12 or IL-12 is a heterodimeric cytokine (comprising an approximately 35 kD subunit ("p35") and an approximately 40 kD subunit ("p40"), which was originally identified as a factor which induces γ-interferon from T cells and natural killer cells, as set forth in PCT/US91/06332, published Apr. 2, 1992, which is incorporated herein by reference. PCT/US91/06332 refers to IL-12 as Natural Killer Cell Stimulating Factor or NKSF. EP 433827, published Jun. 26, 1991 discloses IL-12 as a cytotoxic lymphocyte maturation factor (CLMF). These patent publications also disclose the cloning and expression of IL-12 and its subunits. Thus, through advances in recombinant DNA technology, it has been possible to produce IL-12 protein.

Interleukin-12 also stimulates natural killer cells in vitro by increasing their ability to lyse target cells at a level comparable to that obtained with interferon-α and interleukin-2, well-known activators of natural killer cells' cytotoxic activity. Additional in vitro activities of interleukin-12 which have been identified include induction of T cell proliferation as a co-stimulant; suppression of interleukin-2 induced proliferation of natural killer blasts; suppression of interleukin-2 induced proliferation of T cell receptor-γδ-positive cells; promotion of Th1 T cell differentiation from progenitors; enhancement of Th1, but not Th2 proliferation; enhancement of T cell cytolytic activity; enhancement of cytotoxic lymphocyte generation; enhancement of natural killer and natural killer blast cytolytic activity; ex vivo enhancement of natural killer activity in peripheral blood mononuclear cells of interleukin-2-treated patients; induction of adhesion molecules on natural killer cells; induction of perforin and granzyme B mRNAs in natural killer blasts; induction of interleukin-2 receptor subunits (p55, p75) on natural killer cells; induction of low levels of tumor necrosis factor-α; suppression of IgE synthesis by interferon-γ-dependent and independent mechanisms; modulation of T cell development in fetal thymic organ cultures; and synergy with kit ligand to promote growth of myeloid and B cell progenitors. The known in vivo activities of interleukin-12 include induction of interferon-γ; enhancement of natural killer cell activity in spleen, liver, lungs and peritoneal cavity; enhancement of generation of allo-specific cytotoxic lymphocytes; induction of extramedullary hematopoiesis in mouse spleen; reversible suppression of hematopoiesis in bone marrow; reversible induction of anemia, lymphopenia, and neutropenia in mice; suppression of anti-IgD induced IgE, IgG1, and interleukin-4 expression; increased survival in SCID mice treated with *Toxoplasma gondii;* cure of leishmaniasis in susceptible strains of mice; decreased bioburden in cryptococcoses model; suppression of tumor growth; and promotion of immunity to tumor cells. Interleukin-12 is also induced in vivo in the shwarzman reaction model of septic shock.

In order to provide interleukin-12 for therapeutic purposes it is necessary to purify the material such that it is free of contaminants, such as host cell proteins and viruses. Since interleukin-12 is a heterodimer, it is also necessary to separate the disulfide bonded dimer from its unassociated individual subunits, particularly the p40 subunit which is abundantly expressed. Therefore, it would be desirable to provide a method of purifying interleukin-12 which satisfies these goals.

SUMMARY OF THE INVENTION

Preferred embodiments of the present invention provide a method for purification of IL-12 comprising loading a composition containing said IL-12 onto a hydrophobic interaction chromatography (HIC) resin and eluting said IL-12 from said HIC resin.

In other embodiments, the method further comprising at least one additional step selected from the group consisting of:

(a) loading a solution containing IL-12 onto an anion exchange resin and eluting said IL-12 from said anion exchange resin;

(b) loading a solution containing IL-12 onto a cation exchange resin and eluting said IL-12 from said cation exchange resin;

(c) concentrating a solution containing IL-12 by tangential-flow ultrafiltration; and (d) loading a solution containing IL-12 onto a size exclusion resin and eluting said IL-12 from said size exclusion resin;

wherein said additional step is performed either prior to loading of said composition onto said HIC resin or after elution of said IL-12 from said HIC resin.

In particularly preferred embodiments, the method comprises the following steps in the following order:

(a) loading a solution containing IL-12 onto an anion exchange resin and eluting said IL-12 from said anion exchange resin;

(b) loading the eluate of step (a) onto a cation exchange resin and eluting said IL-12 from said cation exchange resin;

(c) loading the eluate of step (b) onto a hydrophobic interaction chromatography (HIC) resin and eluting said IL-12 from said HIC resin;

(d) concentrating the eluate of step (c) by tangential-flow ultrafiltration; and (e) loading the concentrate from step (d) onto a size exclusion resin and eluting said IL-12 from said size exclusion resin.

Other preferred embodiments of the invention provide a method for purification of IL-12 comprising the following steps:

(a) loading a solution containing IL-12 onto an anion exchange resin and eluting said IL-12 from said anion exchange resin; and (b) loading a solution containing IL-12 onto a cation exchange resin and eluting said IL-12 from said cation exchange resin;

wherein said steps are performed in any order. In some embodiments, the anion exchange step is performed prior to the cation exchange step, while the cation exchange step is performed prior to the anion exchange step in others. Such methods may further comprise the step of loading a composition containing said IL-12 onto a hydrophobic interaction chromatography (HIC) resin and eluting said IL-12 from said HIC resin, wherein the HIC resin step is performed either before or after the ion exchange steps.

The product of the purification methods of the present invention may me used to make compositions comprising IL-12. Preferred compositions comprise IL-12 and a pharmaceutically acceptable carrier.

DETAILED DESCRIPTION OF THE INVENTION

Figure 1:
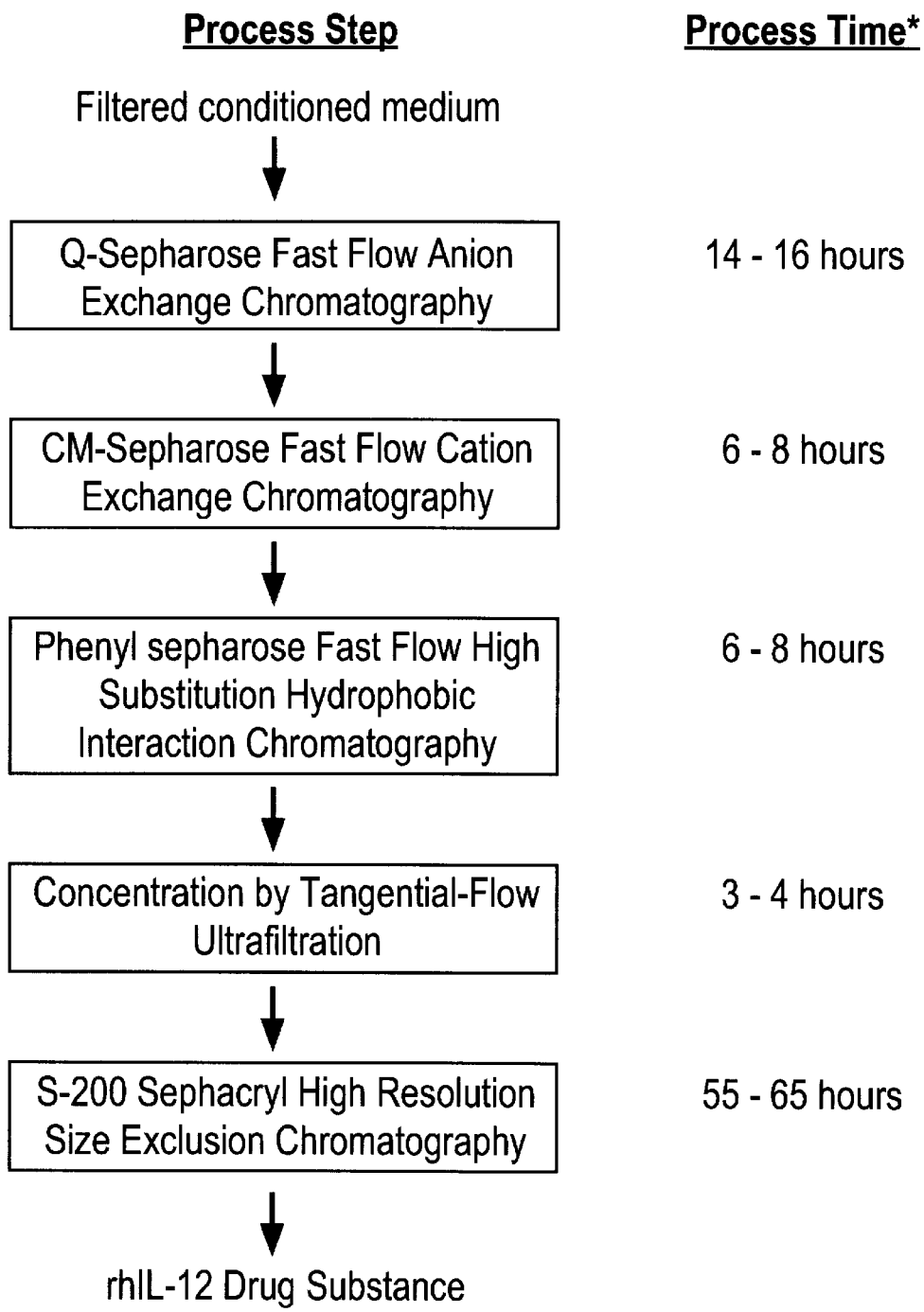
FIG. 1 is a flowchart summarizing a preferred embodiment the rhIL-12 purification process of the present invention.

The methods of the present invention are useful for purification of any form of IL-12, its subunits or biologically active fragments thereof (collectively referred to herein as "IL-12"). When IL-12 is a heterodimer, the 40 kD subunit has substantial homology to the 40 kD subunit of human IL-12 as set forth in PCT/US91/06332 and is disulfide bonded to a 35 kD subunit having substantial homology to the 35 kD subunit of human IL-12 as set forth in that same PCT publication. "Substantial homology" means greater than 75% homology at the amino acid level, while retaining the ability to treat the desired condition in a mammalian subject. Another form of IL-12 which may be used in the present invention is an IL-12 subunit. Such an IL-12 40 kD subunit has substantial homology to the human IL-12 40 kD subunit disclosed in PCT/US91/06332, and such an IL-12 35 kD subunit has substantial homology to the human IL-12 35 kD subunit disclosed in such PCT publication. Fragments of the IL-12 subunits that retain IL-12 biological activity are also useful for purification in accordance with the present invention.

It is preferable to recombinantly produce IL-12 for purification by the methods of the present invention, through expression of DNA sequences encoding one or both of the IL-12 subunits in a suitable transformed host cell. For example, using known methods the DNA sequences encoding human IL-12 set forth in PCT/US91/06332 may be linked to an expression vector such as pED (Kaufman et al., Nucleic Acids Res. 19, 4484–4490(1991)). In such an expression vector, sequences which optimize translation such as CCACC (Kozak, M., Nucleic Acids Res. 12, 857–871 (1984)) may be added 5' to the initiation codon using known methods. The expression vector containing the IL-12 subunits may then be transformed into a host cell, and protein expression may be induced and maximized, to produce heterodimeric human IL-12. For production of heterodimeric IL-12,the DNA sequences encoding the IL-12 subunits may be present on different expression plasmids or present in tandem on a single expression plasmid.

When a subunit or fragment of IL-12 is used to practice the present invention, it may also be produced recombinantly using known methods. For example, the DNA sequence encoding the human IL-12 40 kD subunit set forth in PCT/US91/06332 may be linked to an expression vector, transformed into a host cell, and expression induced and maximized to produce the human IL-12 40 kD subunit. Similarly, the DNA sequences encoding the human IL-12 35 kD subunit as set forth in the PCT publication may be linked to an expression vector, transformed into a host cell, and expression induced and maximized to produce the corresponding protein. Of course, degenerate DNA sequences encoding the IL-12 subunits may also be employed to produce IL-12 for use in the present invention, as can DNA sequences encoding allelic variants of the IL-12 subunits. Chemically or genetically modified forms of IL-12 and its subunits can also be made in accordance with the methods disclosed in the PCT publication.

Any suitable expression vector may be employed to produce IL-12 for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJL4 (Gough et al., EMBO J. 4, 645–653 (1985)); and pMT2 (derived from pMT2-VWF, A.T.C.C. #67122; see PCT/US87/00033). Suitable expression vectors for use in yeast, insect, and bacterial cells are also known. Construction and use of such expression vectors is well within the level of skill in the art.

Suitable host cells for recombinant production of IL-12 useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 3–46 (1981)), baby hamster kidney cells, and the like. IL-12 may also be produced by transformation of yeast, insect, and bacterial cells with DNA sequences encoding the IL-12 subunits, induction and amplification of protein expression, using known methods.

IL-12 may be purified from culture medium or extracts of cells which naturally produce the protein according to the present invention.

Pharmaceutical compositions containing IL-12 purified in accordance with the present invention may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

It is currently contemplated that the various pharmaceutical compositions should contain about 0.1 micrograms to about 1 milligram of IL-12 per milliliter.

Administration of such compositions can be carried out in a variety of conventional ways. Intravenous, intramuscular, cutaneous or sub-cutaneous injection may be employed for administration. For injection, IL-12 will preferably be administered in the form of pyrogen-free, parenterally acceptable aqueous solutions. The preparation of such parenterally acceptable protein solutions, having due regard to pH, isotonicity, stability and the like, is within the skill of the art.

The amount of IL-12 used for treatment will depend upon the severity of the condition, the route of administration, the activity of the IL-12, and ultimately will be decided by the treatment provider. In practicing the methods of treatment of this invention, a therapeutically effective amount of IL-12 is administered. The term "therapeutically effective amount" means the total amount of each active component of the method or composition that is sufficient to show a meaningful patient benefit (e.g., curing, ameliorating, delaying or preventing onset of, preventing recurrence or relapse of the condition treated). One common technique to determine a therapeutically effective amount for a given patient is to administer escalating doses periodically until a meaningful patient benefit is observed by the treatment provider. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of IL-12 in this invention is contemplated to be in the range of about 0.001 to about 1000 µg/kg. The number of administrations may vary, depending on the individual patient and the severity of the treated condition.

As used herein, the term "IL-12" includes both murine and human interleukin-12, unless otherwise specified.

The methods of the present invention are further described in the following examples, which are intended to illustrate the invention without limiting its scope.

EXAMPLES

The following examples describe a preferred embodiment of the present invention for purification of recombinant human IL-12 (rhIL-12). The methods disclosed and claimed herein can also be applied to purification of IL-12 from other sources.

Section 1 Facility

Four of the five purification steps were performed in a cold room that was maintained at 2° to 8° C. The Phenyl Sepharose® FF HS step was performed in the purification area that was maintained at 18° to 24° C. A biosafety cabinet in the purification area was used for filtering the product pool from the last purification step into bottles for storage of rhIL-12.

Section 2 Purification Process Overview

The purification of rhIL-12 occurred in five steps (FIG. 1). In the cell culture area, the filtered conditioned medium was diluted 1:1 (vol:vol) in bulk with the Q Sepharose® FF column equilibration buffer. The diluted filtered medium was then transferred to the cold room in the purification area where it was loaded onto the first column in the purification process, a Q Sepharose® FF anion-exchange chromatography column. After an acidic (pH 5.5) wash step, the column was washed with equilibration buffer. Then rhIL-12 was eluted from the column in a step-wise manner with a solution containing sodium chloride as the eluent.

In the second step, the Q Sepharose® FF column eluate was diluted 1:4 (vol:vol) in bulk with the equilibration buffer for the CM Sepharose® FF column and was loaded onto the CM Sepharose® FF cation-exchange chromatography column under mildly acidic conditions (pH 6.0). After a wash step at pH 7.2 the rhIL-12 was eluted from the CM Sepharose® FF column in a step-wise manner with a solution containing sodium chloride as the eluent.

In preferred embodiments, as a third step, the CM Sepharose® FF column eluate was diluted 1:1 (vol:vol) in bulk with a 2× concentrate of the Phenyl Sepharose® FF HS equilibration buffer, and loaded onto the Phenyl Sepharose® FF HS hydrophobic interaction chromatography (HIC) column. The column was first washed with equilibration buffer, followed by a wash containing isopropanol to remove excess p40, and then a wash with equilibration buffer to remove the isopropanol prior to elution. The rhIL-12 was eluted from the column in a step-wise manner with a low ionic strength buffer. In certain other embodiments, this Phenyl Sepharose® FF HS HIC Step is not performed.

In the fourth step, the Phenyl Sepharose® FF HS eluate was concentrated by tangential-flow ultrafiltration using a spiral-wound membrane cartridge to approximately 2% of the S-200 Sephacryl® HR column bed volume in preparation for gel-permeation chromatography. This step can also be performed with a higher ionic strength buffer.

In the fifth step, the concentrated retentate from the tangential-flow ultrafiltration step was applied to the S-200 Sephacryl® HR column, which had been equilibrated previously with phosphate-buffered saline. The rhIL-12 was then eluted with equilibration buffer and collected by weight in bulk. This step can also be performed at an increased ratio of load to volume and at a faster flow rate.

The S-200 Sephacryl® HR eluate of rhIL-12 was diluted to a concentration of approximately 2.5 mg/ml with phosphate-buffered saline, filtered (0.2 µm), sampled, labeled, frozen and stored at −80° C.

Section 3 Raw Materials Used in the Purification of rhIL-12

The raw materials used in the purification of the rhIL-12 are listed in Table 3-1. Tables 3-2 through 3-8 show the acceptance specifications for the noncompendial raw materials used in the purification of rhIL-12.

TABLE 3-1

Raw Materials Used in the Purification of rhIL-12

| Process step | Raw Material | Grade |
|---|---|---|
| Q Sepharose ® | Q Sepharose ® Fast Flow Resin | noncompendial |
| | Sodium chloride | USP |
| | Hydrochloric acid | NF |
| | L-histidine | USP |
| | Sodium hydroxide | NF |
| | Tromethamine [Tris (hydroxymethyl) aminomethane] | USP |
| | Tris (hydroxymethyl) aminomethane hydrochloride | noncompendial |
| | Acetic acid, glacial | USP |
| CM Sepharose ® | CM Sepharose ® Fast Flow resin | noncompendial |
| | Sodium chloride | USP |
| | 2-(N-morpholino) ethanesulfonic acid sodium salt | noncompendial |
| | 2-(N-morpholino) ethanesulfonic acid | noncompendial |
| | Monobasic sodium phosphate | USP |

TABLE 3-1-continued

Raw Materials Used in the Purification of rhIL-12

| Process step | Raw Material | Grade |
|---|---|---|
| | monohydrate | |
| | Dibasic sodium phosphate heptahydrate | USP |
| | Sodium hydroxide | NF |
| Phenyl Sepharose ® | Phenyl Sepharose ® 6 fast flow/high substitution resin | noncompendial |
| | Monobasic sodium phosphate monohydrate | USP |
| | Dibasic sodium phosphate heptahydrate | USP |
| | Ammonium sulfate | ACS |
| | Isopropyl alcohol | USP |
| | Sodium chloride | USP |
| | Sodium hydroxide | NF |
| Concentration | Monobasic sodium phosphate monohydrate | USP |
| | Dibasic sodium phosphate heptahydrate | USP |
| | Sodium chloride | USP |
| | Sodium hydroxide | NF |
| Sephacryl ® S-200 | Sephacryl ® S-200 high resolution resin | noncompendial |
| | Sodium chloride | USP |
| | Sodium hydroxide | NF |
| | Potassium chloride | USP |
| | Monobasic potassium phosphate | NF |
| | Dibasic sodium phosphate heptahydrate | USP |

USP = United States Pharmacopeia
NF = National Formulary
ACS = American Chemical Society Reagent Chemicals
Sephacryl ® and Sepharose ® are registered trademarks of Pharmacia

TABLE 3-2

Specifications for Q Sepharose ® Fast Flow Resin

| | |
|---|---|
| Description: | Macroporous, bead formed, strong anion exchanger based on highly cross-linked Sepharose ® 6B of high chemical and physical stability. Supplied as a suspension in 20% ethanol. |
| Formula: | N/A |
| Formula Weight: | N/A |

| Characteristic | Specification |
|---|---|
| Appearance | white to off-white slurry |
| Microscopic appearance | beads of similar size aud shape |
| Approximate resin volume | report results |
| Total capacity (mmll Cl/mL gel) | 0.18–0.25 |
| Flow rate at 100 KPa | 400–700 cm/hour |
| Particle size distribution (% volume within 45–165 microns) | ≧80.0% |
| Function test Separation of: | elution volume (mL) |
| Transferrin | 57–83 |
| Ovalbumin | 104–136 |
| β-lactoglobulin | 161–195 |

TABLE 3-3

Specifications for CM Sepharose ® Fast Flow Resin

| | |
|---|---|
| Description: | Macroporous, bead formed, weak cation exchanger based on highly cross-linked Sepharose ® 6B of high chemical and physical stability. Supplied as a suspension in 20% ethanol. |
| Formula: | N/A |
| Formula weight: | N/A |

| Characteristic | Specification |
|---|---|
| Appearance | white to off-white slurry |
| Approximate resin volume | report results |
| Total capacity (mmol H*/mL gel) | 0.09–0.13 |
| Function[a] (molarity of salt concentration in elution peak) | M NaCl |
| α-chymotrypsinogen | 0.10–0.15 |
| Cytochrome C | 0.15–0.21 |
| Lysozyme | 0.22–0.29 |
| Particle size distribution (% volume between 45–165 microns) | ≧80% |
| Flow rate at 100 KPa (bed height 14–16 cm) | 300–600 cm/hour |

TABLE 3-4

Specifications for Sephacryl ® S-200 High Resolution Resin

| | |
|---|---|
| Description: | A gel filtration matrix prepared by covalently cross-linking allyldextran with N,N-methylenebisacrylamide; supplied as a suspension in 20% ethanol. |
| Formula: | N/A |
| Formula Weight: | N/A |

| Characteristic | Specification |
|---|---|
| Appearance | white to off-white slurry |
| Flow rate at 100 Kpa (bed height 14–16 cm) | ≧150 cm/hour |
| Particle size distribution (% volume between 25–75 microns) | ≧90% |
| Selectivity[a] (molecular weight of proteins tested): | partition coefficient ($K_{ay}l$) |
| 100,000 | 0.13–0.23 |
| 50,000 | 0.23–0.33 |
| 10,000 | 0.47–0.57 |
| Unspecified adsorption (mg cytochrome C/100 ml gel bed) | ≦0.6 |

TABLE 3-5

Specifications for Phenyl Sepharose ® 6 Fast Flow/High Sibstitution Resin

| | |
|---|---|
| Description: | A hydrophobic interaction chromatography (HIC) medium obtained by derivatization of cross-linked agarose beads (Sepharose ® 6 fast flow) with phenyl groups. Supplied as a suspension in 20% ethanol. |
| Formula: | N/A |
| Formula weight: | N/A |

| Characteristic | Specification |
|---|---|
| Appearance | white to off-white slurry |
| Approximate resin volume | report results |
| Function test | retention time (minutes) |
| Ribonuclease A | 31–37 |
| Lysozyme | 53–64 |

TABLE 3-6

Specifications for TRIS (hydroxymethyl) Minomethane Hydrochloride

| | |
|---|---|
| Description: | White crystals |
| Formula: | $C_4H_{11}NO_3 \cdot HCl$ |
| Formula Weight: | 157.6 |

| Characteristic | Specification |
|---|---|
| Appearance | white crystals |
| Appearance, liquid | 1% aqueous solution is clear, colorless, and particulate-free |
| IR spectrum | A dispersion in potassium bromide compares to a reference standard spectrum |
| Chloride identification | 1% aqueous solution yields a white precipitate when treated with silver nitrate test solution |
| pH (1% aqueous solution) | 4.0–5.0 |
| Melting point | 147–152° C. |
| Water | ≦2.0% |
| Assay | ≧98.0% |

TABLE 3-7

Specifications tor 2-(N-morpholino) Ethanesulfonic Acid (Free Acid)

| | |
|---|---|
| Description: | White crystals |
| Formula: | $C_8H_{12}NO_4S \cdot H_2O$ |
| Formula Weight | 213.01 |

| Characteristic | Specification |
|---|---|
| Appearance | white crystals |
| Appearance, liquid | 1% aqueous solution is clear and colorless |
| IR spectrum | A dispersion in potassium bromide compares to a reference standard spectrum |
| UV absorbance (0.1 M aqueous solution) | $A_{260}$: ≦0.04 |
| pH (1% aqueous solution) | 3.0–5.0 |
| Water | ≦10.0% |
| Assay (anhydrous basis) | ≧99.5% |

TABLE 3-8

Specifications for 2-(N-morpholino) Ethanesulfonic Acid Sodium Salt

| | |
|---|---|
| Description: | White crystals |
| Formula: | $C_6H_{13}NO_4SNa$ |
| Formula Weight: | 217.2 |

| Characteristic | Specification |
|---|---|
| Appearance | white crystals |
| Solubility | 10% aqueous solution is clear and colorless |
| IR spectrum | A dispersion in potassium bromide compares to a reference standard spectrum |
| Sodium identification | Imparts an intense yellow color to a nonluminous flame |
| UV absorbance (10% aqueous solution) | $A_{260}$: ≦0.05<br>$A_{280}$: ≦0.03 |
| pH (1% aqueous solution) | 8.9–10.1 |
| Water | 5.0–11.0% |
| Assay (anhydrous basis) | >97.0% |

Section 4 Solutions Used in the Purification of the rhIL-12

The composition of each solution used in the purification of the rhIL-12 is described in Table 4-1. The solutions used for operation of the first three column steps in the process, except the elution buffer for the Phenyl Sepharose® FF HS step, were prepared with purified water (meeting USP requirements for Water for Injection). The solutions used in the elution of the Phenyl Sepharose® FF HS column and in the last two steps of the purification process were prepared with Water for Injection. All solutions were stored at 2° to 8° C., except the strip buffer for the Q Sepharose® FF column, elution and regeneration/storage buffer for the Phenyl Sepharose® FF HS step, both buffers for the tangential-flow ultrafiltration step, and the storage buffer for the S-200 Sephacryl® HR column which were stored at 2° to 30° C. Additional exceptions were the equilibration, diluent, and wash buffers for the Phenyl Sepharose® FF HS step which were stored at 18° to 24° C. The buffer solutions were passed through a 0.2-$\mu$m filter before use.

TABLE 4-1

Solutions Used in Purificatian of rhIL-12 Drug Substance

| Purification Step | Procedure | Solution[a] | MFR[b] |
|---|---|---|---|
| Q Sepharose ® FF | equilibration, load diluent, Wash I, Wash III | 0.02 M TRIS, pH 8.0 | 805 |
| | Wash II | 0.04 M histidine, pH 5.5 | 828 |
| | elution | 0.02 M TRIS, 0.2 M NaCl, pH 8.0 | 825 |
| | strip | 0.02 M TRIS, 2.0 M NaCl, pH 8.0 | 823 |
| | Regeneration I, storage | 0.1 M NaOH, 1.0 M NaCl | 614 |
| | Regeneration II | 10% acetic acid | 826 |
| CM Sepharose ® FF | equilibration, load diluent, Wash I | 0.02 M MES, pH 6.0 | 827 |
| | Wash II | 0.02 M sodium phosphate, pH 7.2 | 831 |
| | elution | 0.02 M sodium phosphate 0.2 M NaCl, pH 7.2 | 830 |
| | strip | 0.02 M sodium phosphate, 2.0 M NaCl, pH 7.2 | 829 |
| | storage | 0.1 M NaOH, 1.0 M NaCl | 614 |
| Phenyl-Sepharose ® FF HS | equilibration, Wash I, Wash III | 20 mM sodium phosphate, 1.0 M ammonium sulfate, pH 7.2 | 890 |
| | load diluent | 40 mM sodium phosphate, 2.0 M ammonium sulfate, pH 7.2 | 892 |
| | Wash II | 5% isopropanol, 20 mM sodium phosphate, 1.0 M ammonium sulfate, pH 7.2 | 893 |
| | elution | 20 mM sodium phosphate, 0.1 M NaCl, pH 7.2 purified water | 894 |

TABLE 4-1-continued

Solutions Used in Purificatian of rhIL-12 Drug Substance

| Purification Step | Procedure | Solution[a] | MFR[b] |
|---|---|---|---|
| | strip regeneration, storage | 0.1 N NaOH | 014 |
| Concentration | membrane equilibration, flush | 0.02 M sodium phosphate, 0.1 M NaCl, pH 7.2 | 894 |
| | regeneration | 0.1 N NaOH, 1.0 M NaCl | 819 |
| S-200 Sephacryl ® HR | equilibration, elution | 9.6 mM phosphate in NaCl (8.0 g/L), KCl (0.2 g/L) pH 7.5 | 891 |
| | storage | 0.1 N NaOH, 1.0 M NaCl | 777 |

[a]TRIS = tris(hydroxymethyl)aminomethane
MES = 2-(N-morpholino)ethanesulfonic acid
[b]MFR = Manufacturing Formulation Record.

Section 5 Purification of rhIL-12 by O Sepharose® Fast Flow Anion-Exchange Chromatography Q Sepharose® FF is a strong anion-exchange resin composed of a cross-linked agarose matrix that is covalently derivatized with a quaternary amine group through a short linker. Acidic proteins (such as rhIL-12) and other polyionic substances with a net negative charge at the pH of operation bind to Q Sepharose® FF via charge interactions and were differentially eluted by disruption of these interactions with solutions of increasing ionic strength. This resin was used in the rhIL-12 purification process to adsorb the rhIL-12 from conditioned medium, to remove uncharged and basic contaminants from the process stream, and to deliver a concentrated rhIL-12 process stream into the subsequent cation-exchange process step.

Figure 2:
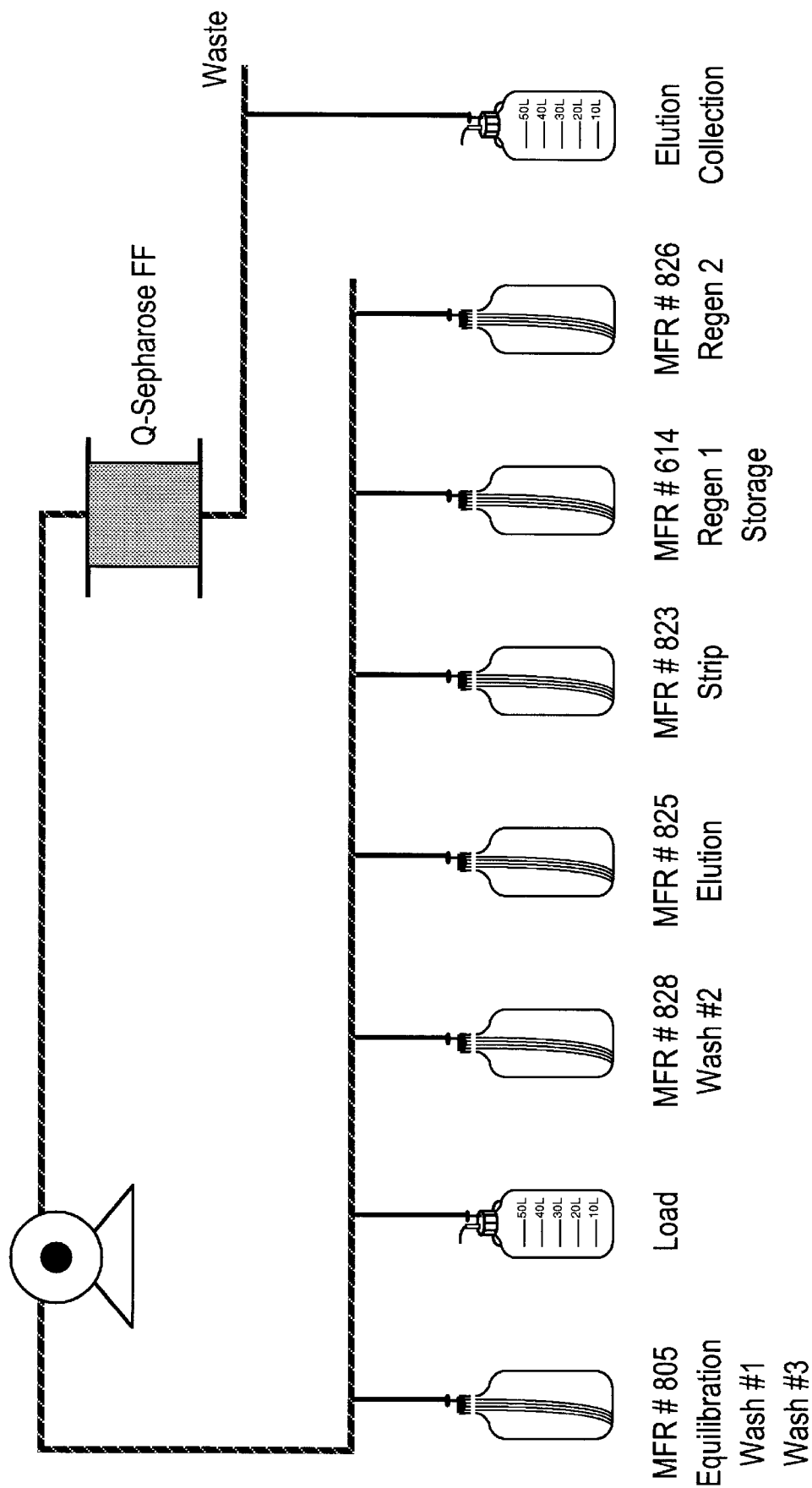
FIG. 2 depicts an overview of the Q Sepharose® Fast Flow Step in preferred embodiments of the present invention.

A schematic diagram of the Q Sepharose® FF chromatography system is presented in FIG. 2. The column operating parameters are listed in Table 5-1. The Q Sepharose® FF column was located in the cold room, and all chromatographic operations for this step were carried out at 2° to 8° C.

The Q Sepharose® FF column was first equilibrated with buffer (MFR 805; 20 mM Tris, pH 8.0). The filtered conditioned medium was chilled to ≦10° C., diluted in-bulk with cold buffer (MFR 805) to a 1:1 ratio (±5 % by volume) and loaded onto the Q Sepharose® FF column. (The temperature of the diluted load was maintained at ≦8° C.)

After the load step was completed, the column was washed with buffer (MFR 805; Column Wash 1) until the UV absorbance of the column effluent equaled that of the wash buffer. This first wash ensured that the filtered conditioned medium had passed through the column and that nonadsorbing impurities in the load had been washed from the system. The column was then washed with buffer (MFR 828; 40 mM histidine, pH 5.5) to remove basic impurities from the resin (Column Wash 2). The column was again washed with buffer (MFR 805; Column Wash 3) to return the column to optimal conditions of pH and conductivity in preparation for elution of the rhIL-12.

The column was eluted with MFR 825 (20 mM Tris, 200 mM NaCl, pH 8.0), and the eluted protein was collected as a single UV-absorbing peak. The Q Sepharose® FF product eluate pool was stored at 2° to 8° C. until further processing.

The endotoxin level, as measured by the Limulus amoebocyte lysate (LAL) test, and the bioburden of the product eluate pool from the Q Sepharose® FF column were monitored to verify sanitary operation. Consistent chromatographic performance was verified by monitoring the elution chromatograms, which were similar for all batches, with the product eluting as a single peak of approximately 2.2 column volumes.

Figure 3:
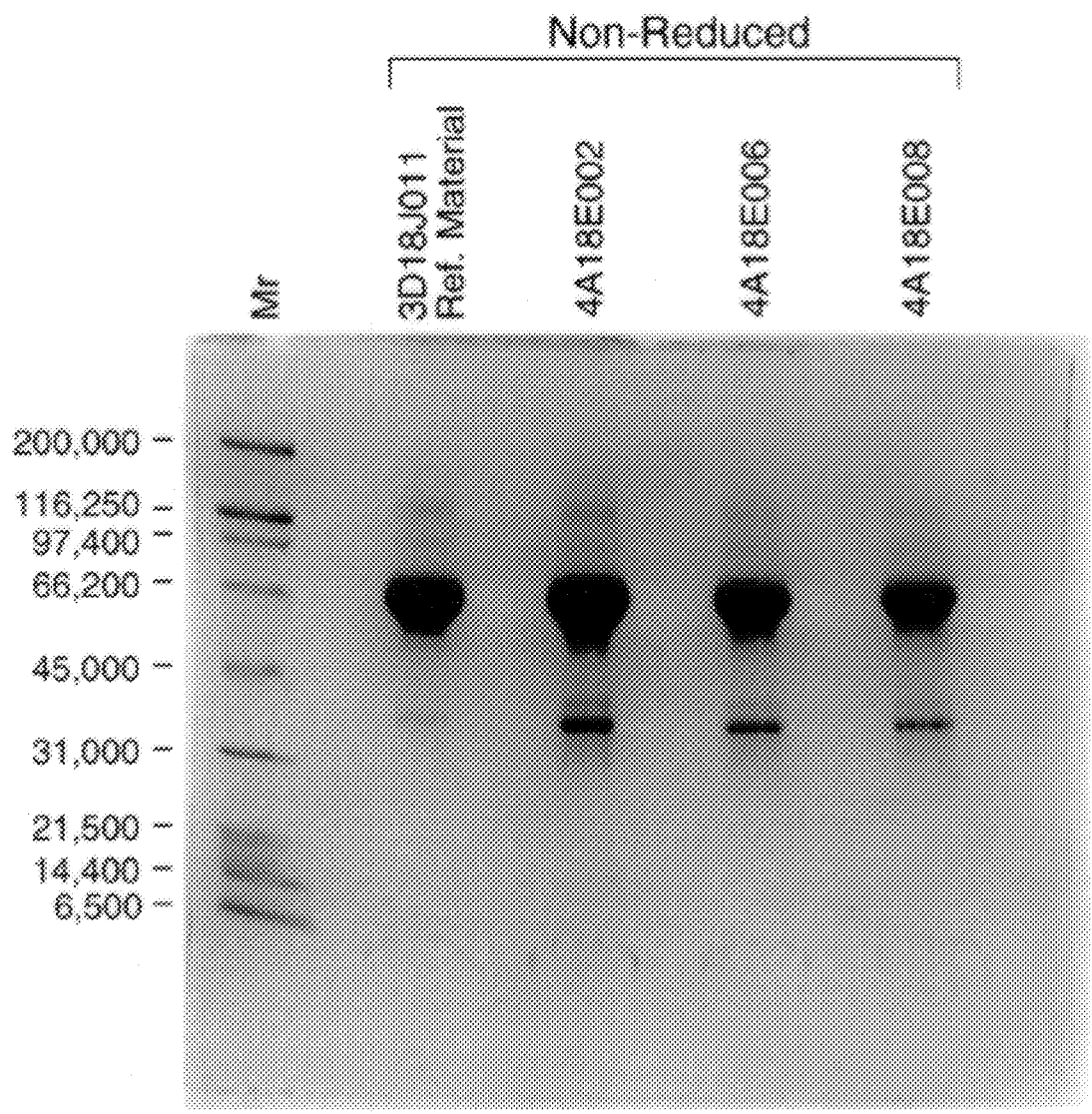
FIG. 3 presents the results of the Q Sepharose® Fast Flow Chromatography Step: SDS-PAGE Analysis (Non-reduced) of In-Process rhIL-12 Batches: Samples were loaded by weight (50 µg/lane) and analyzed by SDS-PAGE (non-reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 5); Lane 6: blank; Lane 7: Batch (as described in example Section 5); Lane 8: blank; Lane 9: Batch (as described in example Section 5); Lane 10: blank.
Figure 4:
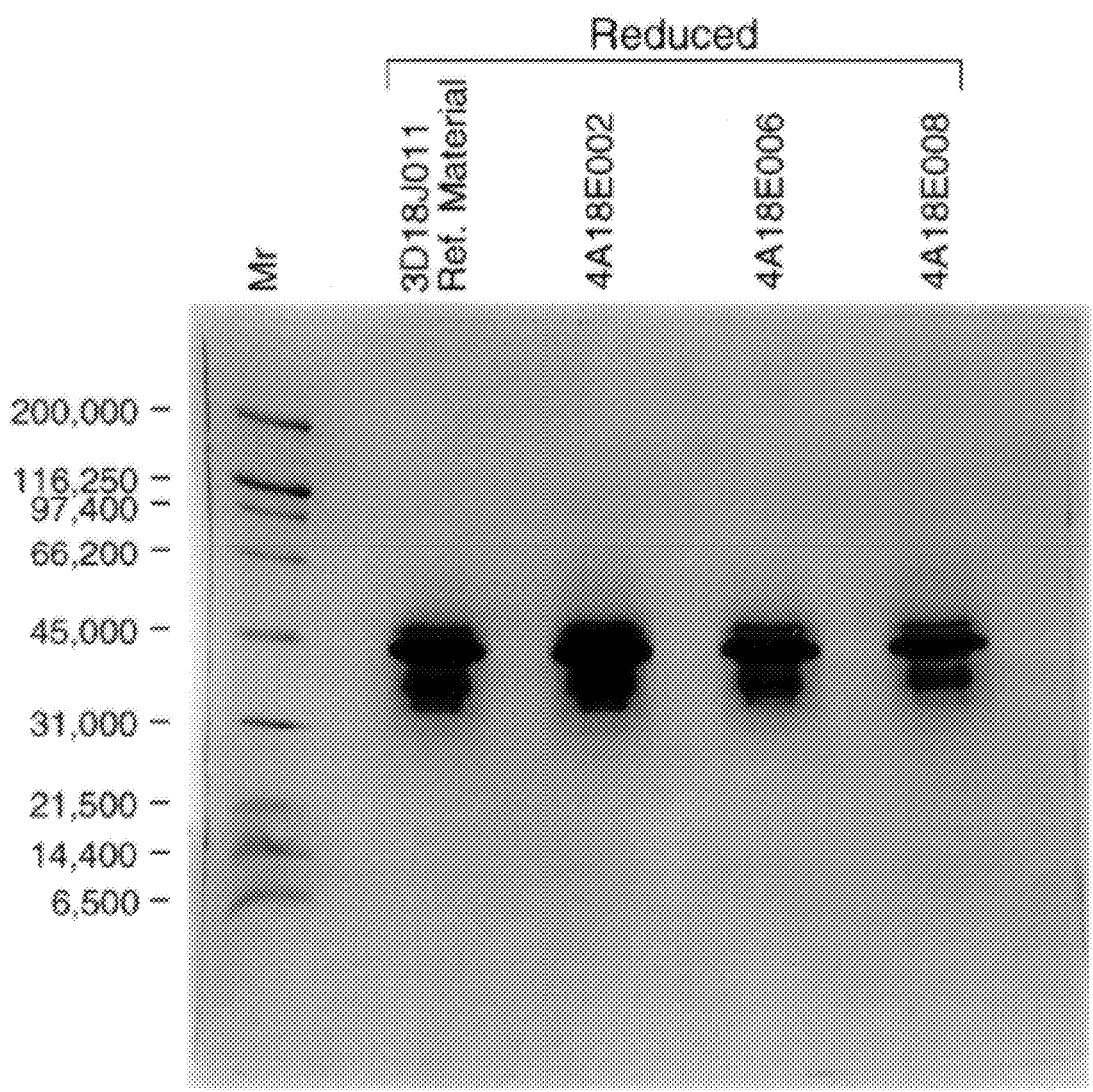
FIG. 4 presents the results of the Q Sepharose® Fast Flow Chromatography Step: SDS-PAGE Analysis (Reduced) of In-Process rhIL-12 Batches: Samples were loaded by weight (50 µg/lane) and analyzed by SDS-PAGE (reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 5); Lane 6: blank; Lane 7: Batch (as described in example Section 5); Lane 8: blank; Lane 9: Batch (as described in example Section 5); Lane 10: blank.

Coomassie-blue-stained SDS-PAGE gels (non-reduced and reduced) of three Q Sepharose® FF product eluate batches and rhIL-12 reference material are presented in FIGS. 3 and 4, respectively. The band patterns of all batches shown were similar by visual inspection. This pattern was also similar to that observed for the rhIL-12 reference material because all prominent bands, even after this first stage of the purification process, are rhIL-12-derived. Together, these observations indicate that the Q Sepharose® FF step consistently yields a product eluate pool of high purity and that the spectrum of rhIL-12 isoforms was consistently represented.

TABLE 5-1

Operating Parameters for the Q Sepharose ® Fast Flow Chromatography Step

| Procedure | Parameter | Recommended Target |
|---|---|---|
| All procedures | pressure | ≦20 psig |
| Column equilibration | column outlet pH | 8.0 |
| | column outlet conductivity | ≦1.5 mS/cm |
| | volume[a] | ≧4.1 column volumes |
| | linear flow rate | ≦2.5 cm/min |
| Load | dilution ratio | 1:1 (buffer to conditioned medium) |
| | pH | 7.6 |
| | conductivity | 5.0 mS/cm |
| | temperature | ≦8° C. |
| | linear flow rate | ≦1.0 cm/min |
| Column Wash 1 | volume[b] | 4.0 column volumes |
| | linear flow rate | ≦2.5 cm/min |
| Column Wash 2 | column outlet pH | 5.5 |
| | column outlet conductivity | ≦3.0 mS/cm |
| | volume[c] | 10 column volumes |
| | linear flow rate | ≦2.5 cm/min |
| Column Wash 3 | column outlet pH | 8.0 |
| | column outlet conductivity | ≦1.5 mS/cm |
| | volume[a] | 4.0 column volumes |
| | linear flow rate | ≦2.5 cm/min |
| Elution | volume | as required |
| | linear flow rate | ≦1.0 cm/min |

[a]Column equilibration and Wash 3 were continued with additional MFR 805 if necessary.
[b]Column Wash 1 was continued with MFR 805 until baseline absorbance was reached.
[c]Column Wash 2 was continued with additional MFR 828 if necessary.

Section 6 Purification of rhIL-12 by CM Sepharose® Fast Flow Cation-Exchange Chromatography CM Sepharose® FF is a weak cation-exchange resin composed of a cross-linked agarose matrix that is covalently derivatized with the carboxymethyl functional group. Basic proteins and polyionic substances with a net positive charge at the pH of operation bind to CM Sepharose® FF via charge interactions and are eluted by disruption of these interactions with solutions of increasing ionic strength. A select subset of acidic proteins (such as rhIL-12) can bind to this resin, presumably through a localized region of net positive charge on the protein surface, and these proteins also are eluted with solutions of increasing ionic strength. The CM Sepharose® FF resin was used in the purification of rhIL-12 to remove from the process stream neutral and acidic contaminants that coelute with rhIL-12 from the Q Sepharose® FF column step.

Figure 5:
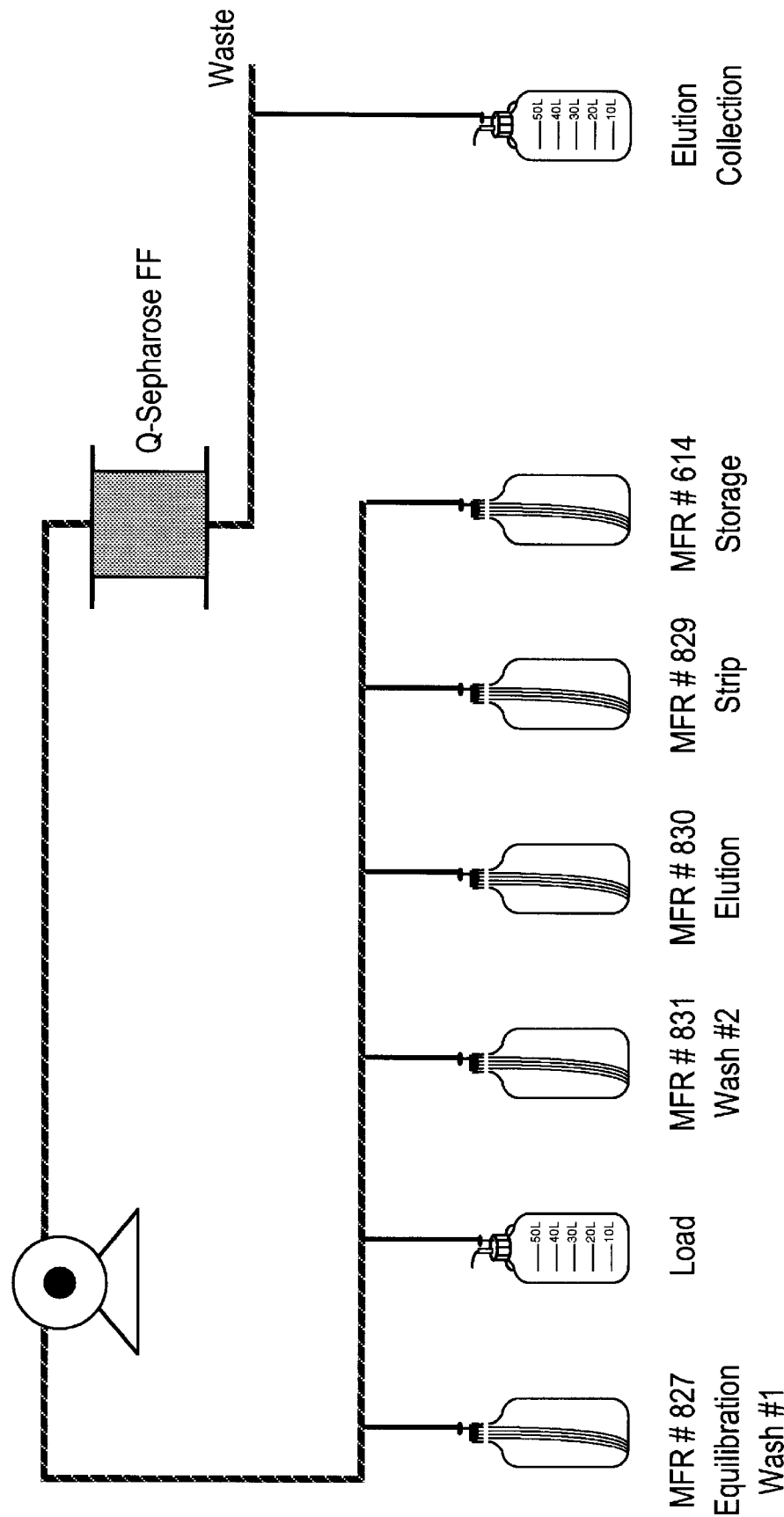
FIG. 5 depicts an overview of the CM Sepharose® Fast Flow Step in preferred embodiments of the present invention.

A schematic diagram of the CM Sepharose® FF chromatography system is presented in FIG. 5. The column operating parameters are listed in Table 6-1. The CM Sepharose® FF column was located in the cold room, and all chromatography operations were carried out at 2° to 8° C.

In preparation for the load step, the CM Sepharose® FF column was equilibrated with MFR 827 (20 mM MES, pH 6.0). The Q Sepharose® FF peak was diluted five-fold (four parts buffer to one part Q Sepharose® FF pool) with MFR 827 in bulk and then loaded onto the column.

The CM Sepharose® FF column was then washed with MFR 827 to ensure that all of the diluted load has passed through the column and that very weakly bound impurities were removed from the column (Column Wash 1). Next, the column was washed with a neutral buffer (MFR 831; 20 mM sodium phosphate, pH 7.2), to remove any additional weakly bound acidic impurities (Column Wash 2).

After the wash steps were completed, the column was eluted with MFR 830 (20 mM sodium phosphate, 200 mM sodium chloride, pH 7.2), and the rhIL-12 product pool was collected as a single UV-absorbing eluate peak. The rhIL-12 eluate pool was stored at 2° to 8° C. until further processing.

The endotoxin level, as measured by the Limulus amoebocyte lysate (LAL) test, and the bioburden of the product eluate pool from the CM Sepharose® FF column were monitored to verify sanitary operation. Consistent chromatographic performance was verified by monitoring the elution chromatograms, which were similar for all batches, with the product eluting as a single peak of approximately 2.0 column volumes.

Figure 6:
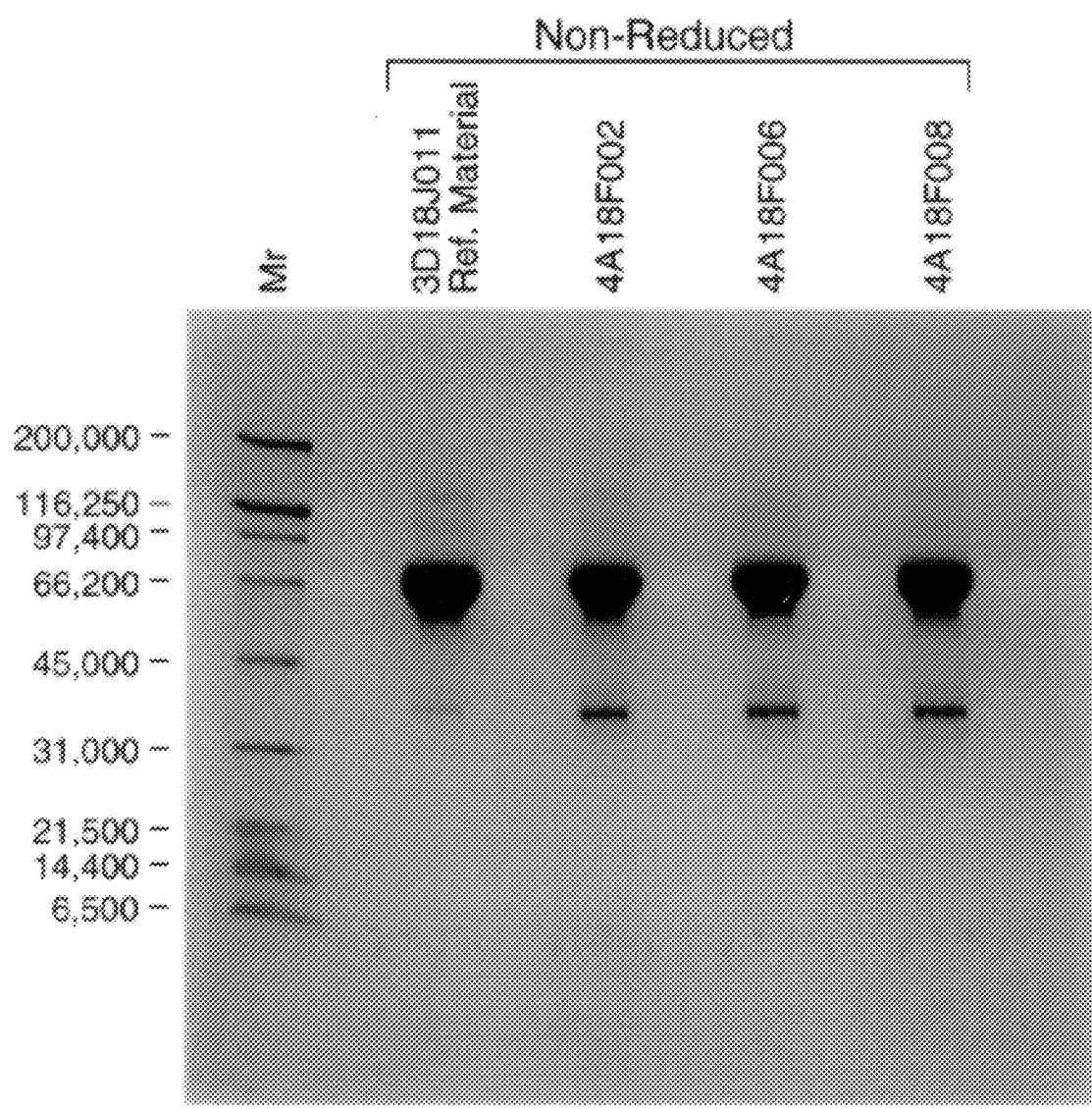
FIG. 6 presents the results of the CM Sepharose® Fast Flow Chromatography Step: SDS-PAGE Analysis (Non-reduced) of In-Process rhIL-12 Batches: Samples were loaded by weight (50 µg/lane) and analyzed by SDS-PAGE (non-reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21, 500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 6); Lane 6: blank; Lane 7: Batch (as described in example Section 6); Lane 8: blank; Lane 9: Batch (as described in example Section 6); Lane 10: blank.
Figure 7:
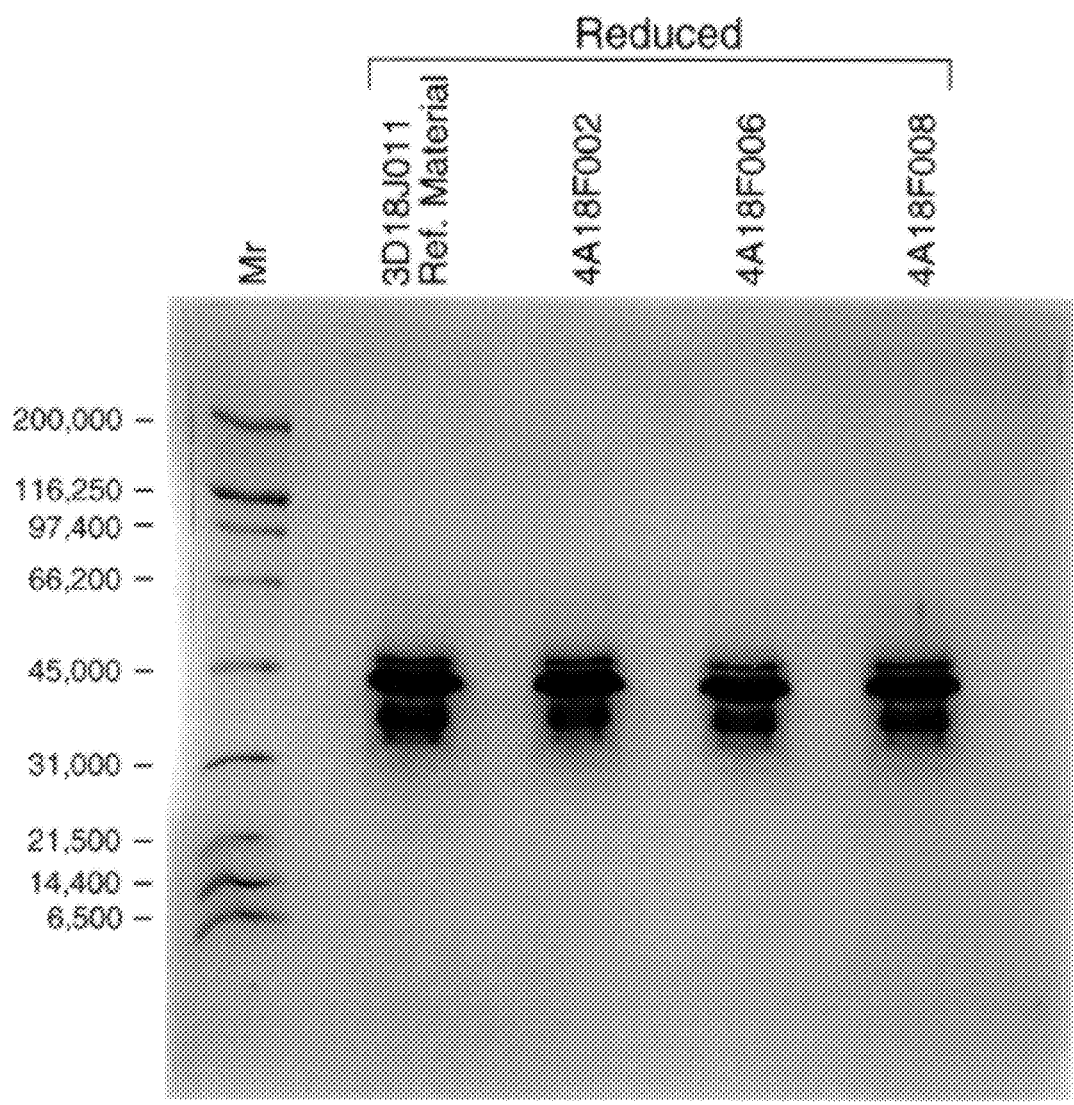
FIG. 7 presents the results of the CM Sepharose® Fast Flow Chromatography Step: SDS-PAGE Analysis (Reduced) of In-Process rhIL-12 Batches: Samples were loaded by weight (50 µg/lane) and analyzed by SDS-PAGE (reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 6); Lane 6: blank; Lane 7: Batch (as described in example Section 6); Lane 8: blank; Lane 9: Batch (as described in example Section 6); Lane 10: blank.

Coomassie-blue-stained SDS-PAGE gels (non-reduced and reduced) of three CM Sepharose® FF product eluate batches and rhIL-12 reference material are presented in FIGS. 6 and 7, respectively. The band patterns of all batches shown were similar by visual inspection. This pattern was also similar to that observed for rhIL-12 reference material, because essentially all bands are rhIL-12-derived. Together, these observations suggest that the CM Sepharose® FF step consistently yields a product eluate pool of high purity and that the spectrum of rhIL-12 isoforms was consistently represented.

TABLE 6-1

Operating Parameters for the CM Sepharose ® Fast Flow Chromatography Step

| Procedure | Parameter | Recommended Target |
| --- | --- | --- |
| All procedures | pressure | ≦20 psig |
| | temperature | ≦8° C. |
| Column equilibration | column outlet pH | 6.0 |
| | column outlet conductivity | ≦1.0 mS/cm |
| | volume[a] | ≧4.0 column volumes |
| | linear flow rate | ≦2.5 cm/min |
| Load | dilution ratio | 4:1 (buffer volume to Q Sepharose FF pool volume) |
| | pH | 6.0 |
| | conductivity | ≦3.5 mS/cm |
| | linear flow rate | ≦2.5 cm/min |
| Column Wash 1 | volume | 10 column volumes |
| | linear flow rate | ≦2.5 cm/min |
| Column | column outlet pH | 7.2 |

TABLE 6-1-continued

Operating Parameters for the CM Sepharose ® Fast Flow Chromatography Step

| Procedure | Parameter | Recommended Target |
| --- | --- | --- |
| Wash 2 | column outlet conductivity | ≦2.0 mS/cm |
| | volume[b] | 5 column volumes |
| | linear flow rate | ≦2.5 cm/min |
| Elution | volume | as required |
| | linear flow rate | ≦1.0 cm/min |

[a]Column equilibration was continued with additionol MFR 827 if necessary.
[b]Column Wash 2 was continued with additional MFR 831 if necessary.

Section 7 Purification of rhIL-12 by Phenyl Sepharose® Fast Flow HS (High Substitution) Chromatography Phenyl Sepharose® Fast Flow HS (high substitution) is a hydrophobic interaction chromatography (HIC) resin consisting of a highly cross-linked 6% agarose hydrophilic matrix covalently derivatized to high density with phenyl groups. Hydrophobic or nonpolar regions on protein surfaces bind to the hydrophobic surface of the resin under conditions of high ionic strength (high salt concentrations) and are eluted by decreasing the ionic strength of the mobile phase. Furthermore, a change in the surface tension of the mobile phase by the addition of water-soluble organic solvents may differentially alter the avidity of proteins that otherwise bind similarly to the resin as a function of ionic strength (such as rhIL-12 heterodimer and excess p40 subunit). In this manner, rhIL-12 heterodimer was separated from excess p40 upon the application of a wash containing 5% isopropanol.

In addition, a host cell protein, MCP-1, was removed from the product stream at this step by adjusting the salt concentration of the load to an ionic strength sufficient for rhIL-12 to bind the resin but insufficient for MCP-1 binding.

Figure 8:
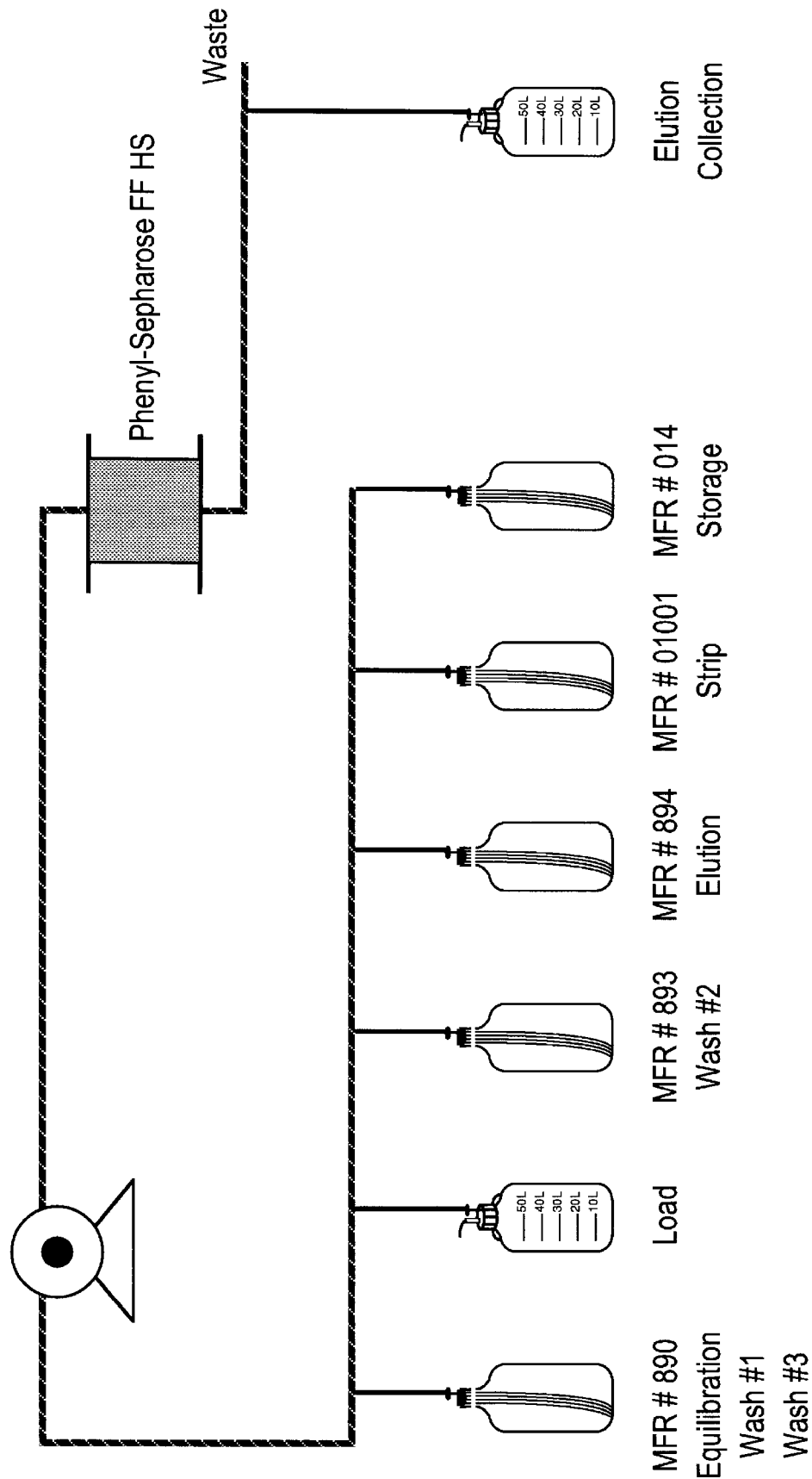
FIG. 8 depicts an overview of the Phenyl Sepharose® Fast Flow HS Step in preferred embodiments of the present invention.

A schematic diagram of the Phenyl Sepharose® FF HS chromatography system is presented in FIG. 8. The column operating parameters are listed in Table 7-1. The Phenyl Sepharose® FF HS column was located in the purification area, and all chromatography operations were carried out at 18° to 24° C., which had been shown to be the optimal temperature range for the performance of this step.

The Phenyl Sepharose® FF HS column was equilibrated with MFR 890 (20 mM sodium phosphate, 1.0M ammonium sulfate, pH 7.2). The CM Sepharose® FF peak was warmed to 18° to 24° C., diluted in bulk with an equal volume of MFR 892 (40 mM sodium phosphate, 2.0M ammonium sulfate, pH 7.2), and then loaded onto the column.

When loading was complete, the column was washed with MFR 890 to ensure that the last of the load has passed through the column and to remove traces of MCP-1 host cell protein (Column Wash 1). Next, the column was washed with a high-salt buffer containing isopropanol (MFR 893; 20 mM sodium phosphate, 1.0M ammonium sulfate, 5% isopropanol, pH 7.2) to remove excess p40 from the adsorbed rhIL-12 heterodimer (Column Wash 2). After the isopropanol wash, a short wash with MFR 890 removed the isopropanol from the column before elution of the rhIL-12 (Column Wash 3).

The column was then eluted with a buffer of relatively low ionic strength (MFR 894; 20 mM sodium phosphate, 0.1M sodium chloride, pH 7.2), and the rhIL-12 product pool was collected as a single UV-absorbing peak. The elution peak was cooled and stored at 2° to 8° C. until further processing.

The endotoxin level, as measured by the Limulus amoebocyte lysate (LAL) test, and the bioburden of the product eluate pool from the Phenyl Sepharose® FF HS column were monitored to verify sanitary operation. Consistent chromatographic performance was verified by monitoring the elution chromatograms; these were similar for all batches, with the product eluting as a single peak of approximately 1.7 column volumes.

Figure 9:
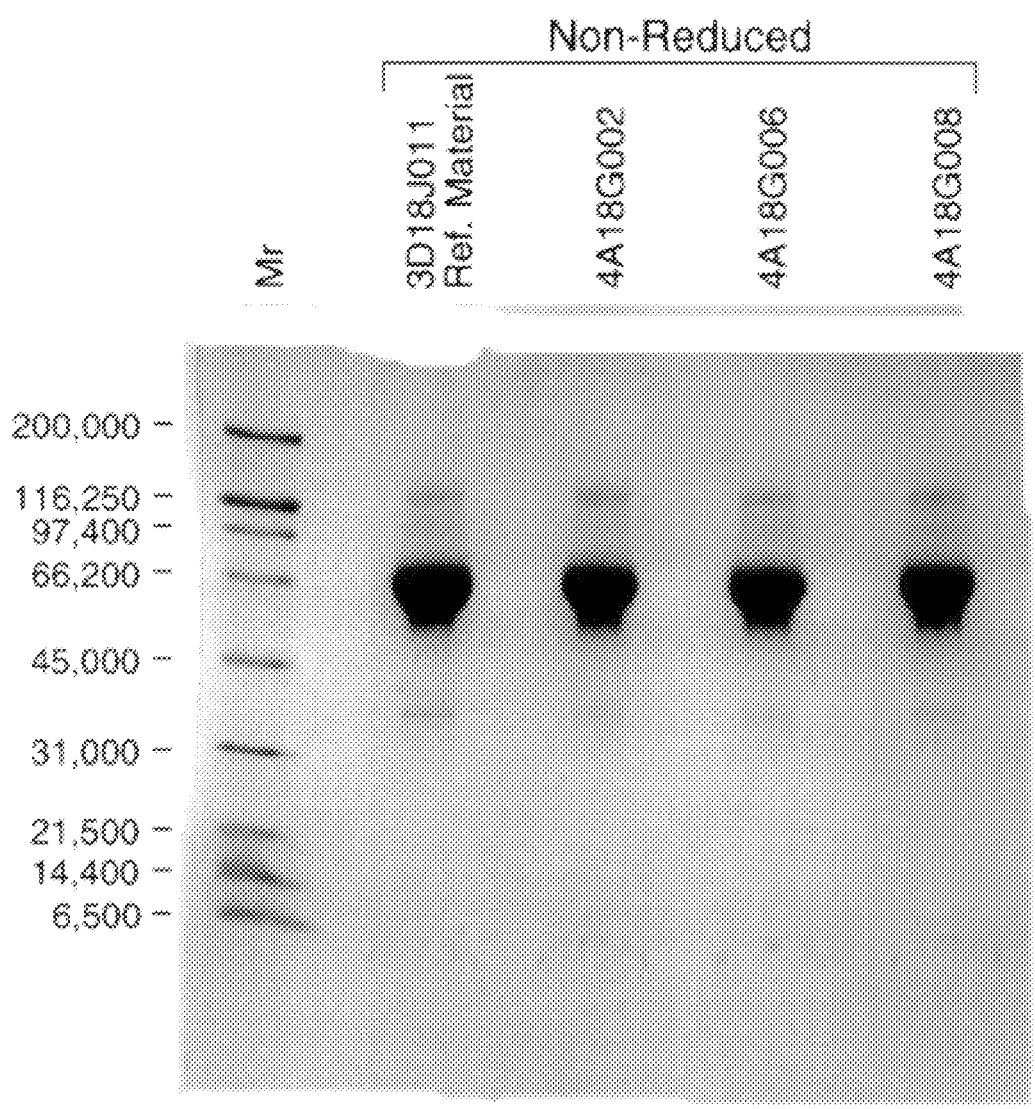
FIG. 9 presents the results of Phenyl Sepharose® Fast Flow HS Chromatography Step: SDS-PAGE Analysis (Nonreduced) of In-Process rhIL-12 Batches: Samples were loaded by weight (50 µg/lane) and analyzed by SDS-PAGE (nonreduced) on a 7 to 20% acrylamide gradient gel. The gel was run in TRIS-glycine buffer at 10° C. at 45 mAmp constant current and then stained with Coomassie blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 7); Lane 6: blank; Lane 7: Batch (as described in example Section 7); Lane 8: blank; Lane 9: Batch (as described in example Section 7); Lane 10: blank.
Figure 10:
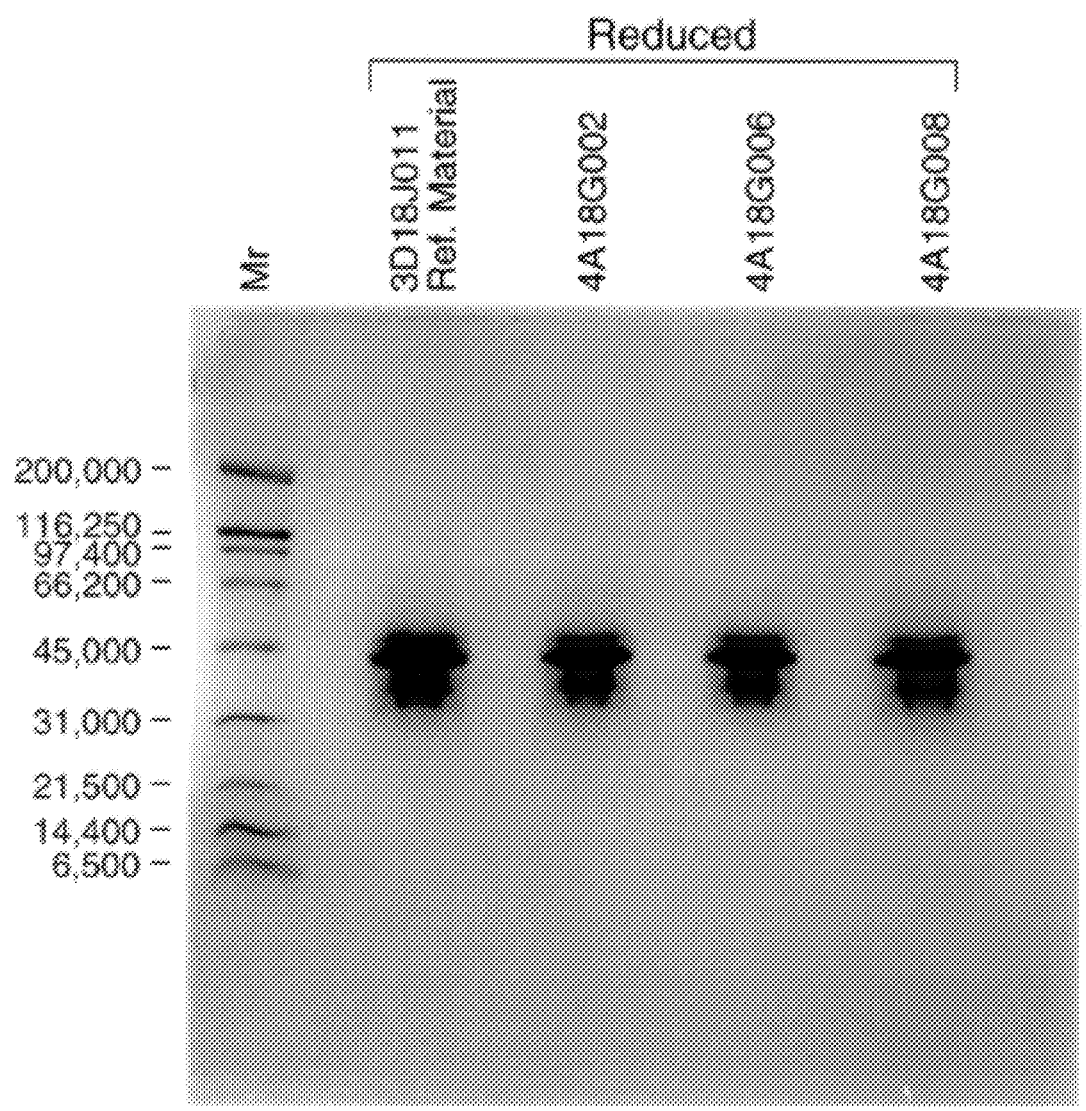
FIG. 10 presents the results of Phenyl Sepharose® Fast Flow HS Chromatography Step: SDS-PAGE Analysis (Reduced) of In-Process rhIL-12 Batches: Samples were loaded by weight (50 µg/lane) and analyzed by SDS-PAGE (reduced) on a 7 to 20% acrylamide gradient gel. The gel was run in TRIS-glycine buffer at 10° C. at 45 mAmp constant current and then stained with Coomassie blue. Lane 1: protein molecular weight markers containing myosin (rabbit skeletal muscle) mw=200,000, β-galactosidase (*E. coli*) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: blank; Lane 5: Batch (as described in example Section 7); Lane 6: blank; Lane 7: Batch (as described in example Section 7); Lane 8: blank; Lane 9: Batch (as described in example Section 7); Lane 10: blank.

Coomassie-blue-stained SDS-PAGE gels (nonreduced and reduced) of three Phenyl Sepharose® FF HS product eluate batches and rhIL-12 reference material are presented in FIGS. 9 and 10, respectively. The band patterns of all batches shown were similar by visual inspection. These patterns were also similar to that observed for rhIL-12 reference material. The band corresponding to the excess p40 may be discerned by SDS-PAGE under nonreducing conditions and was reduced in intensity with respect to the reference material, which was on of the intended effects of this step. Together, these observations suggest that the Phenyl Sepharose® FF HS step consistently yields a product eluate pool of high purity and that the spectrum of rhIL-12 isoforms was consistently represented. Comparison by IEF of the rhIL-12 from prior batches (in which no HIC column was used in the purification process) with material made as described above (using a HIC column) demonstrates that the introduction of this column had no demonstrable effect on the rhIL-12 isoforms in the final rhIL-12.

TABLE 7-1

Operating Parameters for the Phenyl Sepharose ® Fast Flow HS Chromatography step

| Procedure | Parameter | Recommended Target |
|---|---|---|
| All procedures | temperature | 21° C. |
| | pressure | ≦25 psi |
| Column equilibration | column outlet pH | 7.2 |
| | column outlet conductivity | 120 mS/cm |
| | volume[a] | ≧5 column volumes |
| | linear flow rate | ≦2.5 cm/min |
| Load | dilution ratio | 1:1 (buffer to CM Sepharose FF peak pool) |
| | pH | 7.2 |
| | conductivity | 120 mS/cm |
| | linear flow rate | ≦2.5 cm/min |
| Column Wash 1 | column outlet pH | 7.2 |
| | column outlet conductivity | 120 mS/cm |
| | volume[a] | ≧10 column volumes |
| | linear flow rate | ≦2.5 cm/min |
| Column Wash 2 | column outlet pH | 7.2 |
| | column outlet conductivity | 105 mS/cm |
| | volume[b] | ≧10 column volumes |
| | linear flow rate | ≦1 cm/min |
| Column Wash 3 | column outlet pH | 7.2 |
| | column outlet conductivity | 120 mS/cm |
| | volume[a] | ≧3 column volumes |
| | linear flow rate | ≦1 cm/min |
| Elution | volume | as required |
| | linear flow rate | ≦1 cm/min |

[a]Column equilibration, Column Wash 1, and Column Wash 3 were continued with additional MFR 890 if necessary.
[b]Column Wash 2 was continued with additional MFR 893 if necessary.

Section 8 Concentration of rhIL-12 by Tangential-Flow Ultrafiltration

Tangential-flow ultrafiltration is a nonchromatographic separation method that can be used to concentrate and buffer-exchange substances in solution. Tangential-flow ultrafiltration is a continuous-flow method whereby a feedstream is directed parallel to the surface of a semi-permeable membrane. Pressure is applied to the retentate side of the membrane to effect the transport of water and solutes through the membrane on the basis of their relative size and permeability. Lower molecular-weight feedstream components freely pass through the pores of the membrane into the permeate fraction, whereas higher molecular-weight substances (such as rhIL-12) are retained by the membrane and constitute the retentate fraction. In this manner, the Phenyl Sepharose® FF HS elution pool can be concentrated to an appropriate volume for gel permeation chromatography without altering the buffer composition.

Figure 11:
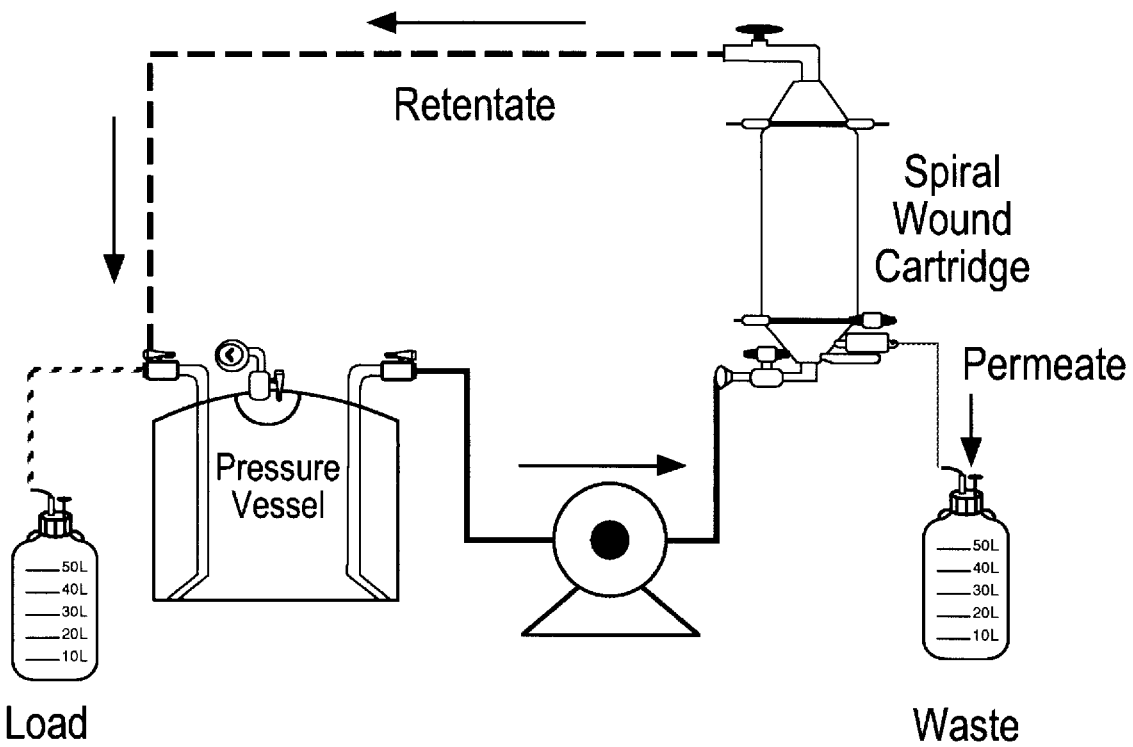
FIG. 11 depicts an overview of the Concentration by Tangential-Flow Ultrafiltration Step in preferred embodiments of the present invention.

A schematic diagram of the tangential-flow ultrafiltration system is presented in FIG. 11. The operating parameters for the tangential-flow filtration step are listed in Table 8-1. The tangential-flow apparatus was located in the cold room, and all operations were carried out at 2° to 8° C.

The spiral-wound cartridge component of the tangential-flow system (Amicon S1Y30 spiral-wound cartridge) was first equilibrated with MFR 894 (20 mM sodium phosphate, 100 mM sodium chloride, pH 7.2), which was also the elution buffer for the Phenyl Sepharose® FF HS column step. In other embodiments 200 mM sodium chloride can be used. The Phenyl Sepharose® FF HS product pool was then transferred to the stainless steel retentate pressure vessel of the tangential-flow apparatus in preparation for protein concentration.

After the transfer was completed, the retentate solution was pumped continuously from the pressure vessel through the spiral-wound cartridge and back to the pressure vessel under a net positive transmembrane pressure. The volume of the retentate was monitored continuously during this operation, using measurements of the permeate fraction.

When the previously determined target permeate volume was reached, the out-flow of the fraction from the retentate pressure vessel was stopped and the retentate fraction in the spiral-wound cartridge was flushed into the retentate pressure vessel with a previously determined volume of equilibration buffer (MFR 894). The concentrated rhIL-12 product pool was recovered from the retentate pressure vessel and was stored at 2° to 8° C. until further processing.

The endotoxin level, as measured by the Limulus amoebocyte lysate (LAL) test, and the bioburden in the concentrated retentate from the tangential-flow ultrafiltration step was monitored to verify sanitary operation. The integrity of the spiral-wound cartridge membrane was evaluated by $A_{280}$ measurement of both the retentate and permeate fractions. Negligible protein was detected in the permeate fraction by this method, confirming that the membrane was intact throughout the operation of this step. The composition of the product concentrate was not expected to change during the tangential-flow ultrafiltration step, since negligible protein was found in the permeate. Hence, SDS-PAGE analysis is not shown for this step, but is included for one representative batch on a gel in Section 10 describing the overall process performance.

TABLE 8-1

Operating Parameters for the Tangential-Flow Ultrafiltration Step

| Procedure | Parameter | Recommended Target |
|---|---|---|
| All procedures | trans cartridge pressure | <5 psig |
| Cartridge equilibration | pH | 7.2 |
| | conductivity | 8 mS/cm |

TABLE 8-1-continued

Operating Parameters for the Tangential-Flow Ultrafiltration Step

| Procedure | Parameter | Recommended Target |
|---|---|---|
| | LAL | <0.125 EU/mL |
| | volume (retentate) | ≧2L |
| | volume (permeate) | ≧200 mL |
| | inlet pressure | 20 psig |
| | retentate flow rate[a] | 1000 mL/min |
| | permeate flow rate[a] | 125 mL/min |
| Concentration | inlet pressure | |
| | first 90% of permeate volume | 20 psig |
| | last 10% of permeate volume | 10 psig |
| | retentate flow rate[a] | |
| | first 90% of permeate volume | 1000 ml/min |
| | last 10% of permeate volume | 500 ml/min |
| | permeate flow rate[a] | |
| | first 90% of permeate volume | 100 ml/min |
| | final permeate volume | load volume - (2% of S-200 column volume) |

[a]Flow rate was based on the use of an Amicon S1Y30 spiral-wound cartridge and can be adjusted for equivalent membrane systems as appropriate.

Section 9 Purification of rhIL-12 by S-200 Sephacryl® High-Resolution Size-Exclusion Chromatography S-200 Sephacryl® HR is a mechanically rigid and stable gel permeation resin. The resin is composed of allyl dextran that is cross-linked in a controlled manner with N,N'-methylene bisacrylamide to yield specified pore sizes. Solutes are separated on the basis of their abilities to diffuse through the pores of the resin, which generally correlate with solute Stoke's radius. A protein solution, such as the concentrated Phenyl Sepharose® FF HS product pool from the rhIL-12 purification process, is applied to the column and then eluted with application buffer. Molecules smaller than rhIL-12 reside for a longer time in the mobile phase within the resin and elute after rhIL-12, whereas molecules larger than rhIL-12 reside for a longer time in the mobile phase outside the resin and elute before rhIL-12. In this manner, contaminants can be removed from the rhIL-12 drug product stream on the basis of their relative molecular weights.

Figure 12:
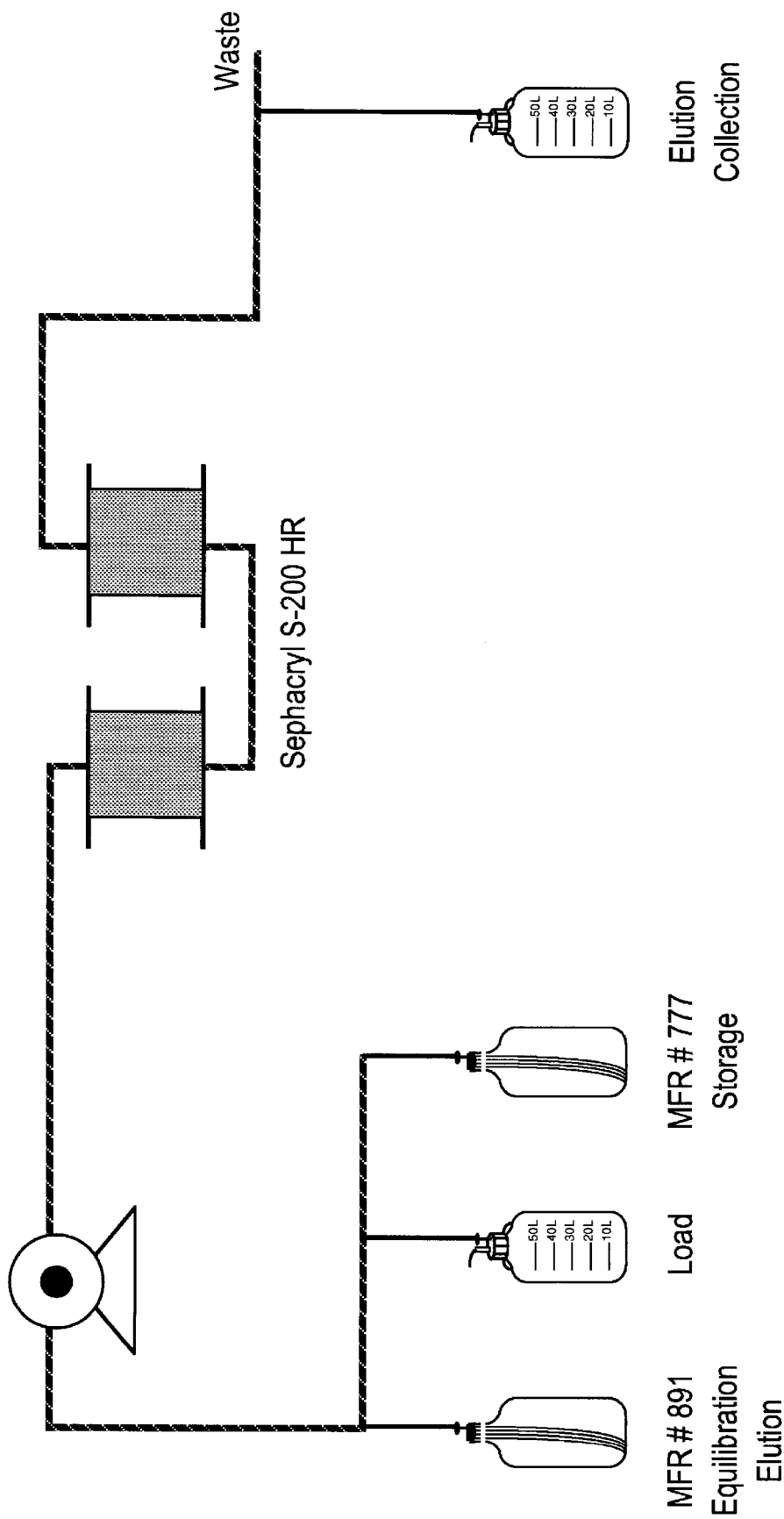
FIG. 12 depicts an overview of the S-200 Sephacryl HR Step in preferred embodiments of the present invention.

A schematic diagram of the S-200 Sephacryl® HR size-exclusion chromatography column is presented in FIG. 12. The operating parameters for this purification step are listed in Table 9-1. The S-200 Sephacryl® HR column was located in the cold room, and all chromatography operations were carried out at 2° to 8° C.

The S-200 Sephacryl® HR column was first equilibrated with MFR 891 [9.6 mM phosphate in NaCl (8.0 g/L), KCl (0.2 g/L) in WFI, pH 7.5 to 7.7]. The concentrated rhIL-12 solution from the tangential-flow ultrafiltration step was then loaded onto the S-200 Sephacryl® HR column. The column was eluted with buffer (MFR 891) at a targeted linear flow rate of 2.6 cm/hr. The column eluate was initially collected in fractions for individual purity analysis. The product eluate pool was then identified using fractions that met specified purity targets. These product eluate pool fractions were then shown to correlate consistently with a defined column eluate volume, and the product peak has since been collected by weight in bulk.

The product eluate pool was diluted to approximately 2.5 mg/mL, filtered through a 0.2-μm bacterial retentive filter, sampled, and aliquotted into 100 mL or 1.0 L depyrogenated Teflon bottles. The rhIL-12 was then frozen quickly in liquid nitrogen and stored at −80° C.

The endotoxin level, as measured by the Limulus amoebocyte lysate (LAL) test, and the bioburden of the product eluate pool from the S-200 Sephacryl® HR column was monitored to verify sanitary operation. Consistent chromatographic performance was verified by monitoring the elution chromatograms, which were similar for all batches, consisting of a symmetrical elution peak within a defined elution volume. All protein detectable by SDS-PAGE analysis or analytical reversed-phase chromatography were rhIL-12 related.

In other batches, the procedures for this step were modified by reduction of the load volume from 5 to 2% of the column volume, and a decrease in the linear flow rate from 10 cm/hr during the load and 20 cm/hr during the elution, to 2.6 cm/hr throughout the column operation.

TABLE 9-1

Operating Parameters for the S-200 Sephacryl ® HR Step

| Procedure | Parameter | Recommended Target |
|---|---|---|
| Column equilibration | pH | 7.5 |
| | conductivity | 10.5 mS/cm |
| | volume[a] | ≧3 column volumes |
| | linear flow rate | ≦17.3 cm/hr |
| | LAL | ≦0.125 EU/mL |
| Load | linear flow rate | 2.6 cm/hr |
| Elution | volume | as required |
| | linear flow rate | 2.6 cm/hr |

[a]Column equilibration was continued with additional MFR 891 if necessary.

Section 10 Performance of the rhIL-12 Purification Process

Figure 13:
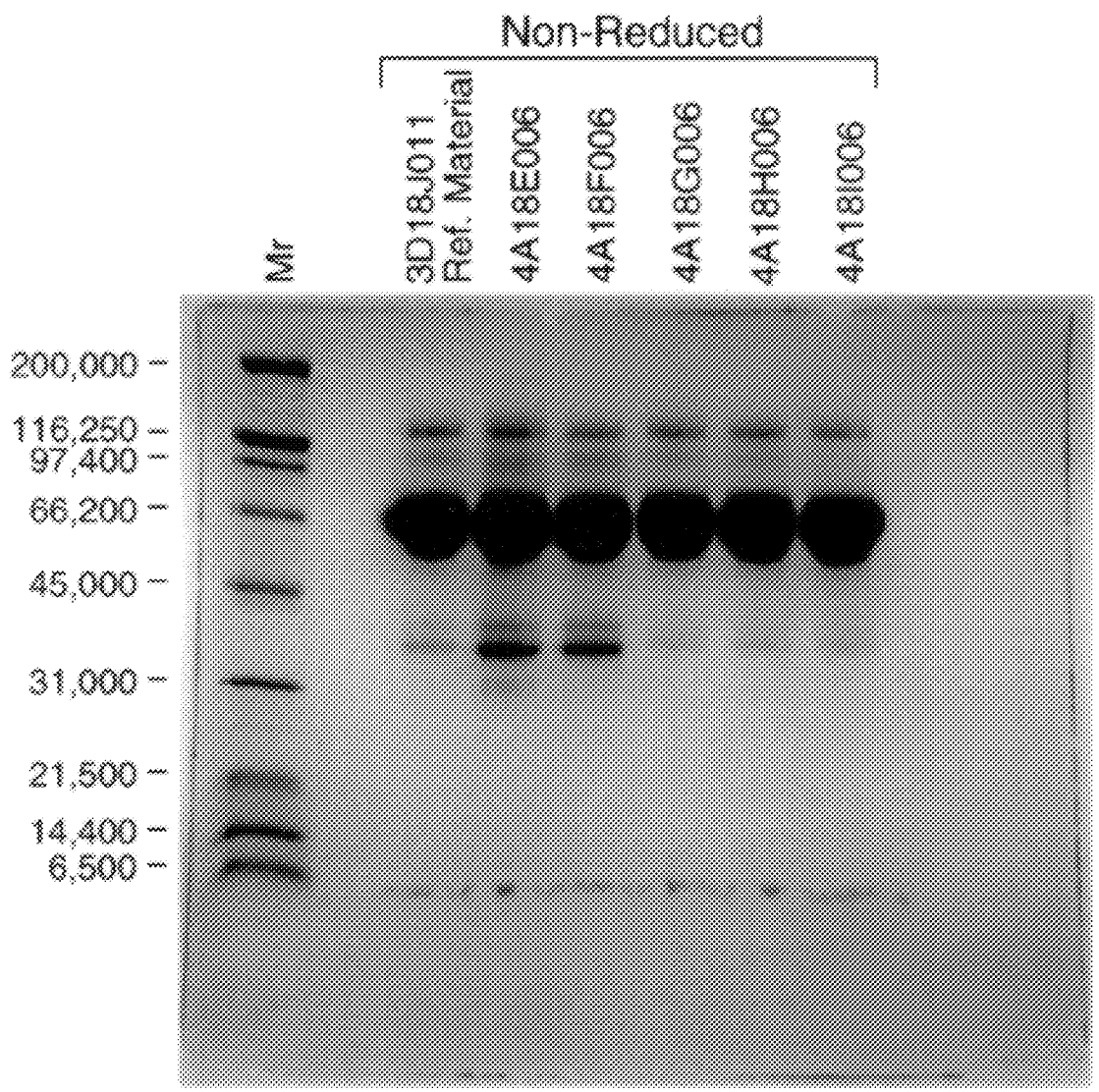
FIG. 13 presents the results of Performance of Purification Process Steps: SDS-PAGE Analysis (Non-reduced) of Batch Through the Purification Process: Samples were loaded by weight (50 µg/lane) and analyzed by SDS-PAGE (non-reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (E. coli) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: Batch (Q Sepharose® FF elution pool); Lane 5: Batch (CM Sepharose® FF elution pool); Lane 6: Batch (Phenyl Sepharose® FF HS elution pool); Lane 7: Batch (Tangential-flow Ultrafiltration retentate); Lane 8: Batch (S-200 Sephacryl HR elution pool); Lane 9: blank; Lane 10: blank.
Figure 14:
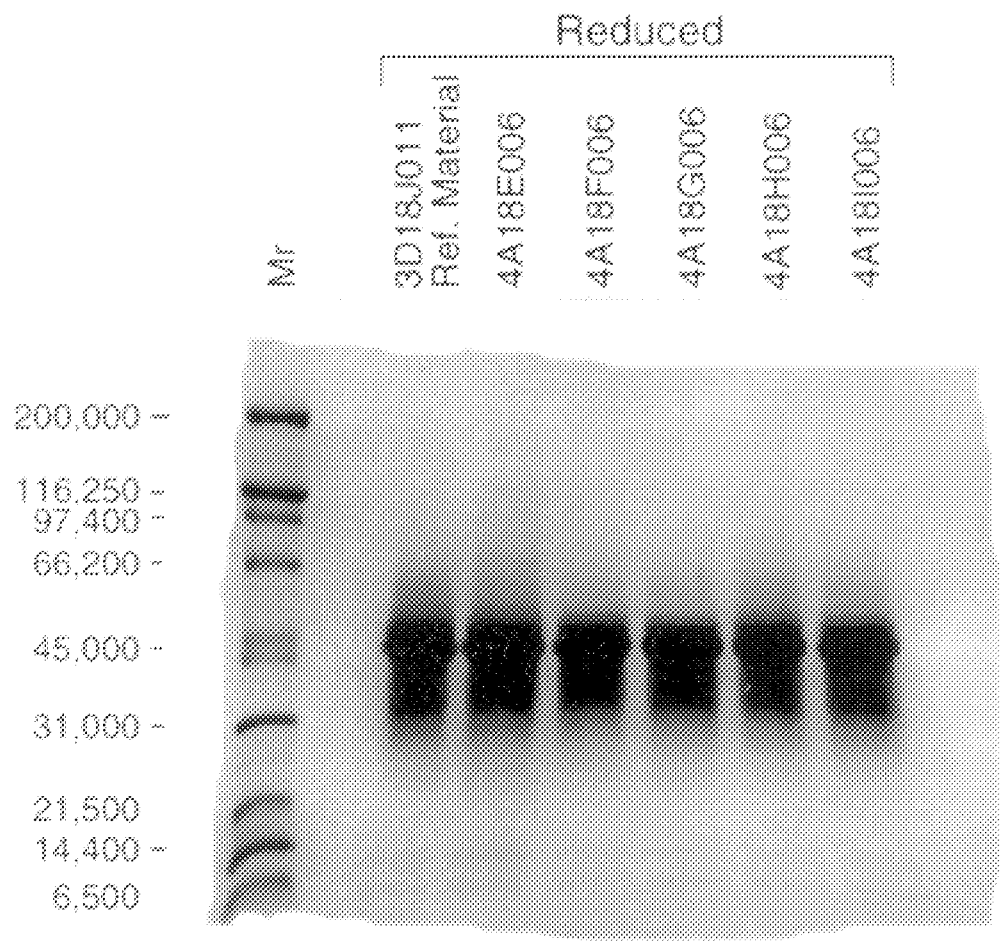
FIG. 14 presents the results of Performance of Purification Process Steps: SDS-PAGE Analysis (Reduced) of Batch Through the Purification Process: Samples were loaded by weight (50 µg/lane) and analyzed by SDS-PAGE (reduced) on a 7 to 20% acrylamide gradient gel. The gel was run in Tris-glycine buffer at 10° C. at 45 mAmp constant current and then stained with Coomassie-blue. Lane 1: protein molecular weight markers containing myosin (rabbit skeletal muscle) mw=200,000, β-galactosidase (E. coli) mw=116,250, phosphorylase B (rabbit skeletal muscle) mw=97,400, serum albumin (bovine) mw=66,200, ovalbumin (chicken) mw=45,000, carbonic anhydrase (bovine) mw=31,000, trypsin inhibitor (soybean) mw=21,500, lysozyme (chicken) mw=14,400, and aprotinin (bovine pancreas) mw=6,500; Lane 2: blank; Lane 3: rhIL-12 reference material; Lane 4: batch (Q Sepharose® FF elution pool); Lane 5: Batch (CM Sepharose® FF elution pool); Lane 6: Batch (Phenyl Sepharose® FF HS elution pool); Lane 7: Batch (Tangential-flow Ultrafiltration retentate); Lane 8: Batch (S-200 Sephacryl® HR elution pool); Lane 9: blank; Lane 10: blank.

Purification of rhIL-12 from filtered conditioned cell culture medium was accomplished with four chromatographic separation steps and a tangential-flow ultrafiltration step, the purpose of which was primarily concentration. These steps were designed to complement each other in removing non-rhIL-12 impurities while retaining the spectrum of rhIL-12 isoforms. The performance of each step in the purification process, as analyzed by SDS-PAGE, is presented in FIGS. 13 and 14.

rhIL-12 was first recovered and concentrated from filtered conditioned cell culture medium using Q Sepharose® FF anion exchange chromatography. The product eluate pool derived from this step was predominantly composed of rhIL-12, as shown by comparison of the SDS-PAGE protein patterns of Q Sepharose® in-process samples for three separate batches with that of purified rhIL-12 reference material (FIGS. 3 and 4), and comparison of in-process samples through the purification process (FIGS. 13 and 14).

The second step of the purification process, CM Sepharose® FF cation-exchange chromatography, further removes trace protein impurities from the rhIL-12 product stream. The CM Sepharose® FF column binds rhIL-12 at pH 6.0, which would not be predicted on the basis of the negative net charge of the protein. Hence, the mode of interaction of rhIL-12 with the CM Sepharose® FF resin was protein structure-specific and was expected to complement the Q Sepharose® FF anion exchange step. (Acidic protein impurities were expected not to bind to CM Sepharose® FF under the conditions used and, hence, were expected to be separated from rhIL-12. Conversely, basic protein impurities were expected not to bind to Q Sepharose® FF and, hence, were expected to be separated from rhIL-12). This complementary effect was further enhanced by a neutral pH wash of the CM Sepharose® FF column before elution (Column Wash 2). The spectrum of rhIL-12 isoforms was unchanged through this step, as evidenced by comparison of the SDS-PAGE protein patterns of CM Sepharose® FF eluate pool samples with those of Q Sepharose® FF eluate pool samples (FIGS. 13 and 14).

The CM Sepharose® FF elution pool was diluted for loading onto the Phenyl Sepharose® FF HS column into a buffer containing ammonium sulfate at a concentration sufficient to bind rhIL-12 to the column, but not high enough to bind the MCP-1 host cell protein contaminant. By taking advantage of this window of ammonium sulfate concentration, MCP-1 protein was removed from the product stream to a level below detection by reversed phase chromatographic analysis. Excess p40, which tracks with rhIL-12 through the first two steps in the process, was also greatly reduced at this column step by applying a wash containing 5% isopropanol and ammonium sulfate, as shown in FIG. 13. (Most of the excess p40 elutes from the column under Wash 2 conditions, whereas the rhIL-12 heterodimer remains bound.) As with the first two process steps, the spectrum of rhIL-12 isoforms remains unchanged through the Phenyl Sepharose® FF HS column, as evidenced by comparison of the SDS-PAGE protein patterns of elution pool samples from this step to those from the earlier steps in the process (FIGS. 13 and 14).

The Phenyl Sepharose® FF HS product eluate pool was concentrated by tangential-flow ultrafiltration, with negligible protein loss, and was taken into the S-200 Sephacryl® HR step. This step provides additional removal of excess p40 and high molecular weight forms. The result of the purification process was highly purified rhIL-12 composed of the isoforms that were present in the first step of the process.

What is claimed is:

1. A method for purification of IL-12 heterodimer comprising the following steps in the following order:

(a) loading a solution containing IL-12 heterodimer onto an anion exchange resin at a pH of 8.0, washing the loaded anion exchange resin with a solution of a pH of 5.5, and eluting said IL-12 heterodimer from said anion exchange resin;

(b) loading the eluate of step (a) onto a cation exchange resin at a pH of 6.0, washing the loaded cation exchange resin with a solution of a pH of 7.2, and eluting said IL-12 heterodimer from said cation exchange resin;

(c) loading the eluate of step (b) onto a hydrophobic interaction chromatography (HIC) resin, washing the loaded HIC resin with a solution comprising isopropanol at a concentration sufficient to elude excess p40 subunit of the heterodimer (p40) from said loaded HIC resin without eluting said IL-12 heterodimer, and eluting said IL-12 heterodimer from said HIC resin;

(d) concentrating the eluate of step (c) by tangential-flow ultrafiltration, and (e) loading the concentrate from step (d) onto a size exclusion resin and eluting said IL-12 heterodimer from said size exclusion resin.

* * * * *